United States Patent
Ofili et al.

(10) Patent No.: US 8,234,131 B2
(45) Date of Patent: Jul. 31, 2012

(54) SYSTEM AND METHOD FOR CHRONIC ILLNESS CARE

(75) Inventors: Elizabeth Ofili, Peachtree City, GA (US); Priscilla I. Pemu, Peachtree City, GA (US); Alexander Quarshie, Lawrenceville, GA (US); Priscilla Johnson, Decatur, GA (US); Laura J. Linn, Roswell, GA (US); Dipendra Kaur, Cumming, GA (US); Jacquelyn Ali, Stone Mountain, GA (US)

(73) Assignee: Morehouse School of Medicine, Atlanta, GA (US)

( * ) Notice: Subject to any disclaimer, the term of this patent is extended or adjusted under 35 U.S.C. 154(b) by 405 days.

(21) Appl. No.: 12/502,950

(22) Filed: Jul. 14, 2009

(65) Prior Publication Data

US 2010/0017229 A1      Jan. 21, 2010

Related U.S. Application Data

(60) Provisional application No. 61/080,593, filed on Jul. 14, 2008.

(51) Int. Cl.
*G06Q 100/00*   (2006.01)
*G06Q 50/00*    (2012.01)
*A61B 5/00*     (2006.01)
*G06F 19/00*    (2011.01)

(52) U.S. Cl. .............................................. 705/3; 705/2
(58) Field of Classification Search .................... 705/2–3
See application file for complete search history.

(56) References Cited

U.S. PATENT DOCUMENTS

| | | | | |
|---|---|---|---|---|
| 6,108,635 A * | 8/2000 | Herren et al. | | 705/2 |
| 7,376,700 B1 * | 5/2008 | Clark et al. | | 709/204 |
| 7,756,722 B2 * | 7/2010 | Levine et al. | | 705/2 |
| 2002/0188467 A1 * | 12/2002 | Eke | | 705/2 |
| 2004/0267565 A1 * | 12/2004 | Grube | | 705/2 |
| 2005/0159984 A1 * | 7/2005 | Hirano et al. | | 705/3 |

* cited by examiner

*Primary Examiner* — Robert Morgan
*Assistant Examiner* — Joy Chng
(74) *Attorney, Agent, or Firm* — Ping Wang; Andrews Kurth, LLP

(57) ABSTRACT

In one aspect, the present invention relates to a computerized system programmed for providing care support to at least one patient having at least one chronic illness. In one embodiment, the system includes a medical professional module adapted for receiving, storing, and providing data in communication with at least one medical professional at the point of care, a health coach module adapted for receiving, storing, and providing data in communication with the at least one patient and at least one health coach, a patient module adapted for receiving, storing, and providing data in communication with the at least one patient, and, a public health module adapted for receiving, storing, and providing data in communication with at least one research professional. Each of the medical professional module, health coach module, patient module, and public health module is operatively associated with a corresponding one of the at least one medical professional, at least one health coach, at least one patient, and at least one research professional through a network.

25 Claims, 17 Drawing Sheets

FIG. 2C

MOREHOUSE SCHOOL OF MEDICINE

| Basic Profile | Blood Glucose | Blood Pressure | Cholestrol | HBA1C | Medications | View Data | Curriculum |

209b

Dipendra Kaur          1999          Female          30041          US

Please check the information above. If that is not you please logout and login again.

4/5/2009   10:00   AM

After Meal   Whole Blood

100

215
216

IMAGE — 218

Please enter the test result numbers on your glucometer.

○ mmol  ⦿ mg/dl — 217

Please select the units shown on your glucometer.

[Add Blood Glucose Measurement] — 219

FIG. 2D

| Pages Visited | Time Spent | |
|---|---|---|
| Diabetes Introduction | 4 Minutes 20 Seconds | March 20, 2009 |
| Types of Diabetes - Page 1 | 2 Minutes 30 Seconds | March 23, 2009 |
| Types of Diabetes - Page 3 | 4 Minutes | March 30, 2009 |
| Types of Diabetes 1 | 5 Minutes | April 2, 2009 |
| Lifestyle | 5 Minutes 50 Seconds | April 2, 2009 |
| Diabetes Introduction Video | 5 Minutes | April 4, 2009 |

MOREHOUSE SCHOOL OF MEDICINE

Basic Profile | Types | Symptoms | Prevention | Diagnosis | Management | Monitoring | Medication | Medications | LifeStyle | Complications | View Data | Information Diabetes There are two main types of diabetes:

* Type I Diabetes
* Type II Diabetes

| Former Name | Preferred Names |
|---|---|
| Type I<br>juvenile diabetes<br>insulin-dependent diabetes mellitus | Type I Diabetes |
| Type II<br>adult-onset diabetes<br>noninsulin-dependent diabetes mellitus<br>NIDDM | Type I Diabetes |

241

[ Next ] 242

SYSTEM AND METHOD FOR CHRONIC ILLNESS CARE

CROSS-REFERENCE TO RELATED PATENT APPLICATION

This application claims the benefit, pursuant to 35 U.S.C. §119(e), of U.S. provisional patent application Ser. No. 61/080,593, filed Jul. 14, 2008, entitled "System and Method for Chronic Illness Care" by Elizabeth Odilile Ofili, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The present invention is generally related to care for chronic illness. More specifically, it relates to a computerized system for providing care for chronic illness.

BACKGROUND OF THE INVENTION

As reported by the Institute of Medicine, chronic illness care is extremely variable across practices and physicians. Despite the increasing availability of electronic health records and the pressure to adopt quality care standards, healthcare disparities in chronic illness persist. Data across various patient demographics show that disparate care is most likely to be present among high risk individuals, whose care is often complicated by multiple co morbidities. With increasing cost pressures in healthcare delivery, it is very difficult for a clinician to effectively manage such patients during the limited time allowed for a clinical encounter.

Electronic medical records and databases provide important support for the clinical encounter. However, clinical decision-making at the point of care remains a fragmented, labor-intensive and frequently incomplete process. Consequently, a clinician must often rely on his or her memory or constantly interrupt the encounter to seek clarification from multiple reference sources. Such an impractical approach is further exacerbated when encountering complex patients that have multiple co morbidities. Additionally, there is a continuous need to update the clinical knowledge skills of a clinical physician with new evidence. However, as managed care pressures limit the time frame for the clinical encounter, incomplete or inaccurate decision making often results. Therefore, there is a persistent information gap at the point of care that is most detrimental to high risk patients that have multiple co morbidities, as is the case with patients who have cardiovascular disease, diabetes, and asthma. Moreover, cost-benefit analyses for care decisions are generally artificially derived outside of routine chronic illness care delivery. Such analyses may be based on assumptions that may not hold true for high risk individuals with multiple co morbidities. Generating appropriate risk adjustments for such high risk patients is critically important, particularly in the emerging pay-for-performance economic model of healthcare.

Therefore, a heretofore unaddressed need still exists in the art to address the aforementioned deficiencies and inadequacies.

SUMMARY OF THE INVENTION

In one aspect, the present invention relates to a computerized system programmed for providing care support to at least one patient having at least one chronic illness. In one embodiment, the system includes a medical professional module adapted for receiving, storing, and providing data in communication with at least one medical professional at the point of care, a health coach module adapted for receiving, storing, and providing data in communication with the at least one patient and at least one health coach, a patient module adapted for receiving, storing, and providing data in communication with the at least one patient, and, a public health module adapted for receiving, storing, and providing data in communication with at least one research professional. Each of the medical professional module, health coach module, patient module, and public health module is operatively associated with a corresponding one of the at least one medical professional, at least one health coach, at least one patient, and at least one research professional through a network.

In one embodiment, the system is further programmed for performing at least one of the functions of providing data including at least one of information from electronic medical records associated with the at least one patient, information associated with at least one treatment compliance program for treating the at least one chronic illness, and information associated with the clinical health condition of the at least one patient and receiving data including at least one decision support algorithm for generating at least one care decision for the at least one patient. The at least one decision support algorithm includes at least one of disease-specific national diagnostic guidelines, disease-specific national treatment guidelines, patient-specific medication plans, and clinical care pathways. The possible functions also include receiving an alert when a proposed medication or proposed medication dosage conflicts with a current medication or current medication dosage associated with the at least one patient, receiving data for supporting patient treatment compliance to chronic illness-specific treatment guidelines selected by at least one of the at least one medical professional and the at least one health coach, providing data through the network from at least one of a health monitoring device, mobile electronic device, and user computer, tracking use of patient-specific curriculum by the at least one patient, tracking communication between each of the at least one patient and at least one of another patient, the medical professional, and the health coach, generating cost-benefit information associated with at least one treatment decision selected by at least one of the at least one medical professional and at least one health coach, analyzing patient-specific data; and, receiving data associated with at least one clinical health trial. Each of the medical professional module, health coach module, patient module, and public health module is further operatively associated with at least one data storage means through the network, where the at least one data storage means is adapted for storing data saved by the at least one corresponding medical professional, at least one health coach, at least one patient, and at least one research professional.

In one embodiment, the at least one chronic illness is heart disease, diabetes, or asthma, and the network is at least one of the internet and a mobile electronic device network. The at least one medical professional is a physician, physician assistant, nurse, or nurse practitioner. The data received by at least one of the medical professional module and health coach module includes at least one of information from electronic medical records associated with the at least one patient, information associated with treatment compliance programs for treating the at least one chronic illness, and information associated with the clinical health condition of the at least one patient. The data provided by the medical professional module includes at least one decision support algorithm for generating at least one care decision for the at least one patient at the point of care. The at least one algorithm is based at least in part on at least one of disease-specific national diagnostic guidelines, disease-specific national treatment guidelines, patient-specific medication plans, and clinical care pathways. The medical professional module is further adapted for providing an alert to the at least one medical professional when a proposed medication or proposed medication dosage conflicts with a current medication or current medication dosage associated with the at least one patient. The data provided by the health coach module includes information for supporting patient treatment compliance to chronic illness-specific treatment guidelines selected by at least one of the at least one medical professional and the at least one health coach. The data received by the patient module includes information provided by the at least one patient through the network from at least one of a health monitoring device, mobile electronic device, and user computer. The data provided by the patient module includes at least one visual representation of the clinical health condition of the at least one patient, and the at least one visual representation includes at least one of graphs and charts associated with the clinical health condition of the at least one patient.

In one embodiment, the patient module is further adapted for tracking use of patient-specific curriculum by the at least one patient and is further adapted for tracking communication between the at least one patient and at least one of another patient, the at least one medical professional, and the at least one health coach. The public health module is further adapted for generating cost-benefit information associated with at least one treatment decision selected by at least one of the at least one medical professional and at least one health coach, analyzing patient-specific data, and receiving data associated with at least one clinical health trial. Each of the medical professional module, health coach module, patient module, and public health module is operatively associated with a graphical user interface including controls for selectively receiving, storing, and providing data in the system in response to an action by at least one of the medical professional, the at least one health coach, the at least patient, and the at least one research professional. The at least one health monitoring device is a heart rate monitor, blood pressure meter, peak flow meter, pulse oximeter, pedometer, weighing scale, or glucometer.

In another aspect, the present invention relates to a computerized system programmed for providing care support to at least one patient having at least one chronic illness. In one embodiment, the system includes a representation means for generating at least one visual representation of data to at least one user, where the at least one user is a medical professional, health coach, patient, or research professional, an interface means having interactive user controls for selectively receiving, storing, and providing data in response to actions by the at least one user, an analysis means for analyzing data, a communication means for sending and receiving data to and from the at least one user and programmed for controlling the functions performed by each of the representation means interface means, analysis means, communication means, and a storage means for storing data saved by the at least one user.

The data includes information associated with at least one of the at least one patient and at least one chronic illness, and at least one of the representation means interface means, analysis means, and communication means is operatively associated with the at least one user through a network. The data includes at least one decision support algorithm for generating at least one care decision for the at least one patient at the point of care and at least one visual representation of the clinical health condition of the at least one patient. The interactive user controls are graphical user interface controls displayed on at least one of a user computer or a mobile electronic device. At least one visual representation is generated by the representation means and includes at least one of graphs and charts associated with the clinical health condition of the at least one patient, and is displayed on at least one of a user computer or a mobile electronic device.

In one embodiment, the system further includes an access control means for controlling access to at least one of the representation means interface means, analysis means, communication means, and storage means, based upon the identity of the at least one user as a medical professional, health coach, patient, or research professional. The network is the internet or a mobile electronic device network and at least one of the representation means interface means, analysis means, and communication means is operatively associated with at least one of a user computer or user mobile electronic device through the network, where at least one of the representation means interface means, analysis means, and communication means includes a web-based application.

In yet another aspect, the present invention relates to a method of using a computerized system programmed for providing care support to at least one patient having at least one chronic illness. In one embodiment, the method includes the steps of accessing the computerized system through a network and providing identification designating that the user is a medical professional, health coach, patient, or research professional. The method also includes performing at least one of the steps of providing data including at least one of information from electronic medical records associated with the at least one patient, information associated with at least one treatment compliance program for treating the at least one chronic illness, and information associated with the clinical health condition of the at least one patient, receiving data including at least one decision support algorithm for generating at least one care decision for the at least one patient at the point of care, where the at least one decision support algorithm includes at least one of disease-specific national diagnostic guidelines, disease-specific national treatment guidelines, patient-specific medication plans, and clinical care pathways, receiving an alert when a proposed medication or proposed medication dosage conflicts with a current medication or current medication dosage associated with the at least one patient, receiving data for supporting patient treatment compliance to chronic illness-specific treatment guidelines selected by at least one of the at least one medical professional and the at least one health coach, providing data through the network from at least one of a health monitoring device, mobile electronic device, and user computer, tracking use of patient-specific curriculum by the at least one patient, tracking communication between each of the at least one patient and at least one of another patient, the medical professional, and the health coach, generating cost-benefit information associated with at least one treatment decision selected by at least one of the at least one medical professional and at least one health coach, analyzing patient-specific data, and, receiving data associated with at least one clinical health trial.

In yet another aspect, the present invention relates to a method of using a computerized system programmed for providing care support to at least one patient having at least one chronic illness. In one embodiment, the method includes the steps of accessing the computerized system through a network and providing identification designating that the user is a medical professional. The method also includes performing at least one of the steps of providing data that includes at least one of information from electronic medical records associated with the at least one patient, information associated with at least one treatment compliance program for treating the at least one chronic illness, and information associated with the clinical health condition of the at least one patient, receiving data that includes at least one decision support algorithm adapted for generating at least one care decision for the at least one patient at the point of care, where the at least one decision support algorithm includes at least one of disease-specific national diagnostic guidelines, disease-specific national treatment guidelines, patient-specific medication plans, and clinical care pathways, and, receiving an alert when a proposed medication or proposed medication dosage conflicts with a current medication or current medication dosage associated with the at least one patient. In one embodiment, the method further includes the step of generating at least one care decision for the at least one patient at the point of care.

In yet another aspect, the present invention relates to a method of using a computerized system programmed for providing care support to at least one patient having at least one chronic illness. In one embodiment, the method includes the steps of accessing the computerized system through a network connection and providing identification designating that the user is a health coach. The method further includes performing at least one of the steps of receiving data for supporting patient treatment compliance to chronic illness-specific treatment guidelines selected by at least one of the medical professional and health coach, tracking use of patient-specific curriculum by the at least one patient, and, tracking communication between each of the at least one patient and at least one of another patient, the at least one medical professional, and the at least one health coach. In one embodiment, the method further includes the step of generating at least one decision associated with patient treatment compliance for the at least one patient.

In yet another aspect, the present invention relates to a method for using a computerized system programmed for providing care support for at least one patient having at least one chronic illness. In one embodiment, the method includes the steps of accessing the computerized system through a network and providing identification designating that the user is the at least one patient. The method also includes performing at least one of the steps of providing data associated with the clinical health condition of the at least one patient through the network from at least one of a health monitoring device, mobile electronic device, and user computer, viewing at least one visual representation of the clinical health condition of the at least one patient, viewing patient-specific curriculum, and, communicating with at least one of another patient, the at least one medical professional, and the at least one health coach through the network. In one embodiment, the method further includes at least one of the steps of receiving, generating, and sending at least one of an SMS text message, electronic mail message, and social networking message, where the step of communicating with at least one of another patient, the at least one medical professional, and the at least one health coach utilizes the network connection.

In yet another aspect, the present invention relates to a method for using a computerized system programmed for providing care support to at least one patient having at least one chronic illness, where the system includes a medical professional module adapted for receiving, storing, and providing data in communication with at least one medical professional, a health coach module adapted for receiving, storing, and providing data in communication with the at least one patient and at least one health coach, a patient module adapted for receiving, storing, and providing data in communication with the at least one patient, and a public health module adapted for receiving, storing, and providing data in communication with at least one research professional, and where each of the medical professional module, health coach module, patient module, and public health module is operatively associated with the corresponding at least one medical professional, at least one health coach, at least one patient and at least one research professional through a network connection. In one embodiment, the method includes at least one of the steps of causing the medical professional module to perform at least one of the functions of receiving data, storing data, and providing data, causing the health coach module to perform at least one of the functions of receiving data, storing data, and providing data, causing the patient module to perform at least one of receiving data, storing data, and providing data, and, causing the public health module to perform at least one of receiving data, storing data, and providing data, where the data includes at least one decision support algorithm for generating at least one care decision for the at least one patient at the point of care and at least one visual representation of the clinical health condition of the at least one patient.

In yet another aspect, the present invention relates to a method for using a computerized system that is programmed for providing care support to at least one patient having at least one chronic illness, where the system includes a representation means for generating at least one visual representation of data to at least one user, and where the at least one user is a medical professional, health coach, patient, or research professional. The computerized system also includes an interface means having interactive user controls for manipulating data in response to an action by the at least one user, an analysis means for analyzing data, a communication means for sending and receiving data to and from the at least one user, a storage means for storing data saved by the at least one user, and a network server in communication with and programmed for controlling the functions performed by each of the representation means interface means, analysis means, communication means, and storage means. At least one of the representation means interface means, analysis means, and communication means is operatively associated with the at least one user through a network. In one embodiment, the method includes at least one of the steps of causing the representation means to generate at least one visual representation of data, causing the interactive user controls of the interface means to selectively receive, store, and provide data, causing the analysis means to analyze data, causing the communication means to send and receive data, and, causing the network server to communicate with at least one of the representation means interface means, analysis means, communication means, and storage means, and to control each function of the representation means interface means, analysis means, communication means, and storage means. The data includes information associated with at least one of the at least one patient and at least one chronic illness.

In yet another aspect, the present invention relates to software stored on a computer-readable medium for causing a computing system to perform functions for interacting with at least one user of a system, where the system is programmed for providing care support to at least one patient having at least one chronic illness. In one embodiment, the functions include receiving, storing, and providing data in communication with at least one medical professional, receiving, storing, and providing data in communication with at least one health coach, receiving, storing, and providing data in communication with at least one patient, and, receiving, storing, and providing data in communication with at least one research professional. The data includes at least one decision support algorithm for generating at least one care decision for the at least one patient at the point of care and at least one visual representation of the clinical health condition of the at least one patient.

In yet another aspect, the present invention relates to software stored on a computer-readable medium for causing a computing system to perform functions for interacting with at least one user of a system programmed for providing care support to at least one patient having at least one chronic illness. In one embodiment, the functions include generating at least one visual representation of data to the at least one user, selectively receiving, storing, and providing data in response to an action by the at least one user, analyzing data, sending data, and receiving data to and from the at least one user, and, storing data saved by the at least one user. The data includes information associated with at least one of the at least one patient and at least one chronic illness, and the communication occurs through a network.

BRIEF DESCRIPTION OF THE DRAWINGS

FIG. 2C shows schematically a further illustration of the interface means shown in FIGS. 2A and 2B, according to one embodiment of the present invention.

FIG. 2D shows schematically a further illustration of the interface means shown in FIGS. 2A-2C, according to one embodiment of the present invention.

FIG. 2I shows schematically a further illustration of the interface means shown in FIGS. 2A-2H, according to one embodiment of the present invention.

FIG. 2K shows schematically a further illustration of the interface means shown in FIGS. 2A-2J, according to one embodiment of the present invention.

DETAILED DESCRIPTION OF THE INVENTION

Figure 1:
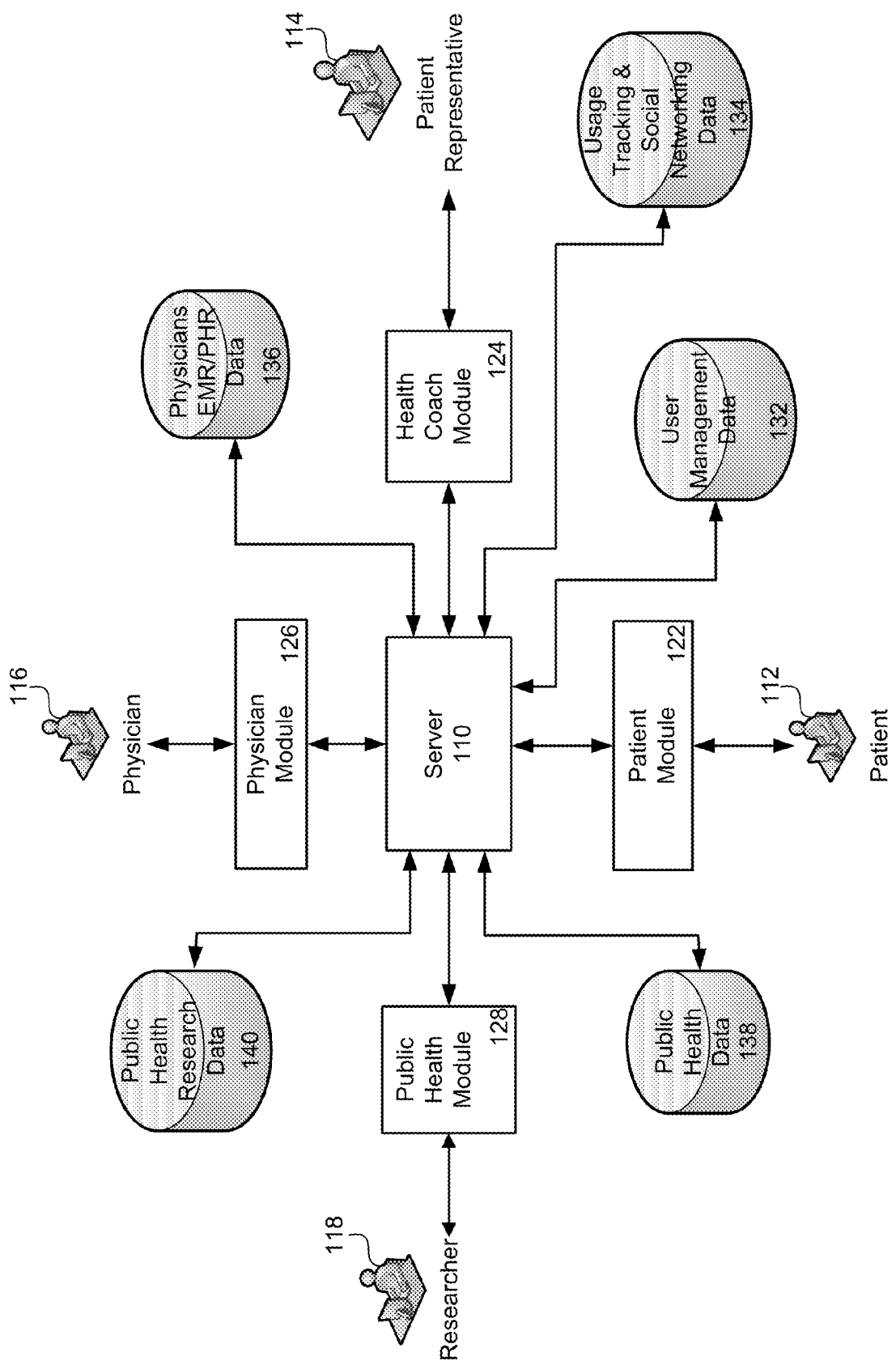
FIG. 1 shows schematically a computerized system for providing care to at least one patient having at least one chronic illness, according to one embodiment of the present invention and the relationship between various users, storage means, and a communication means for the site selection system, according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

Overview of the Invention

The description will be made as to the embodiments of the present invention in conjunction with the accompanying drawings.

Now referring to FIGS. 1-3, in accordance with the purposes of this invention, as embodied and broadly described herein, this invention, in one aspect, relates to a computerized system 100 programmed for providing care support to at least one patient 112 having at least one chronic illness. In one embodiment, the system 100 includes a medical professional module 126 adapted for receiving, storing, and providing data in communication with at least one medical professional 116 at the point of care, a health coach module 124 adapted for receiving, storing, and providing data in communication with the at least one patient 112 and at least one health coach 114, a patient module 122 adapted for receiving, storing, and providing data in communication with the at least one patient 112, and a public health module 128 adapted for receiving, storing, and providing data in communication with at least one research professional 118. Each of the medical professional module 126, health coach module 124, patient module 122, and public health module 128 is operatively associated with a corresponding one of the at least one medical professional 116, at least one health coach 114, at least one patient 112, and at least one research professional 118 through a network 144, 146.

In one embodiment, the system 100 is further programmed for performing at least one of the functions of providing data including at least one of information from electronic medical records associated with the at least one patient 112, information associated with at least one treatment compliance program for treating the at least one chronic illness, and information associated with the clinical health condition of the at least one patient 112, and receiving data including at least one decision support algorithm 300 for generating at least one care decision for the at least one patient 112. The at least one decision support algorithm 300 includes at least one of disease-specific national diagnostic guidelines, disease-specific national treatment guidelines, patient-specific medication plans, and clinical care pathways. The possible functions also include receiving an alert when a proposed medication or proposed medication dosage conflicts with a current medication or current medication dosage associated with the at least one patient 112, receiving data for supporting patient treatment compliance to chronic illness-specific treatment guidelines selected by at least one of the at least one medical professional 116 and the at least one health coach 114, providing data through the network 144, 146 from at least one of a health monitoring device 152, 154, 156, 158, mobile electronic device 148, and user computer 150, tracking use of patient-specific curriculum 238, 241, 244, 247 by the at least one patient 112, tracking communication between each of the at least one patient 112 and at least one of another patient 112, the medical professional 116, and the health coach 114, generating cost-benefit information associated with at least one treatment decision selected by at least one of the at least one medical professional 116 and at least one health coach 114, analyzing patient-specific data, and receiving data associated with at least one clinical health trial. Each of the medical professional module 126, health coach module 124, patient module 122, and public health module 128 is further operatively associated with at least one data storage means 132, 134, 136, 138, 140 through the network 144, 146, where the at least one data storage means 132, 134, 136, 138, 140 is adapted for storing data saved by the at least one corresponding medical professional 116, at least one health coach 114, at least one patient 112, and at least one research professional 118.

In one embodiment, the at least one chronic illness is heart disease, diabetes, or asthma, and the network 144, 146 is at least one of the internet 144 and a mobile electronic device network 146. The at least one medical professional is a physician, physician assistant, nurse, or nurse practitioner. The data received by at least one of the medical professional module 126 and health coach module 124 includes at least one of information from electronic medical records associated with the at least one patient 112, information associated with treatment compliance programs for treating the at least one chronic illness, and information associated with the clinical health condition of the at least one patient 112. The data provided by the medical professional module 126 includes at least one decision support algorithm 300 for generating at least one care decision for the at least one patient 112 at the point of care. The at least one algorithm 300 is based at least in part on at least one of disease-specific national diagnostic guidelines, disease-specific national treatment guidelines, patient-specific medication plans, and clinical care pathways. The medical professional module 126 is further adapted for providing an alert to the at least one medical professional 116 when a proposed medication or proposed medication dosage conflicts with a current medication or current medication dosage associated with the at least one patient 112. The data provided by the health coach module 124 includes information for supporting patient treatment compliance to chronic illness-specific treatment guidelines selected by at least one of the at least one medical professional 116 and the at least one health coach 114. The data received by the patient module 122 includes information provided by the at least one patient 112 through the network 144, 146 from at least one of a health monitoring device 152, 154, 156, 158, mobile electronic device 148, and user computer 150. The data provided by the patient module 122 includes at least one visual representation 201, 204, 208, 214, 225, 232, 235, 237, 240, 243, 246 of the clinical health condition of the at least one patient 112, and the at least one visual representation 201, 204, 208, 214, 225, 232, 235, 237, 240, 243, 246 includes at least one of graphs 223, 230, 234 and charts 222, 229, 236, 241 associated with the clinical health condition of the at least one patient 112.

In one embodiment, the patient module 122 is further adapted for tracking use of patient-specific curriculum 238, 241, 244, 247 by the at least one patient 112 and is further adapted for tracking communication between the at least one patient 112 and at least one of another patient 112, the at least one medical professional 116, and the at least one health coach 114. The public health module 128 is further adapted for generating cost-benefit information associated with at least one treatment decision selected by at least one of the at least one medical professional 116 and at least one health coach 114, analyzing patient-specific data, and receiving data associated with at least one clinical health trial. Each of the medical professional module 126, health coach module 124, patient module 122, and public health module 128 is operatively associated with a graphical user interface 200 including controls 202, 205, 206, 209, 210, 211, 215, 216, 217, 219, 221, 224, 226, 227, 228, 231, 233, 239, 242, 249 for selectively receiving, storing, and providing data in the system 100 in response to an action by at least one of the medical professional 116, the at least one health coach 114, the at least patient 112, and the at least one research professional 118. In one embodiment, the at least one health monitoring device 152, 154, 156, 158 is a heart rate monitor, blood pressure meter, peak flow meter, pulse oximeter, pedometer, weighing scale, or glucometer.

In another aspect, the present invention relates to a computerized system 100 programmed for providing care support to at least one patient 112 having at least one chronic illness. In one embodiment, the system 100 includes a representation means 148, 150 for generating at least one visual representation 201, 204, 208, 214, 225, 232, 235, 237, 240, 243, 246 of data to at least one user 112, 114, 116, 118, where the at least one user 112, 114, 116, 118 is a medical professional 116, health coach 114, patient 112, or research professional 118, an interface means 200 having interactive user controls 202, 205, 206, 209, 210, 211, 215, 216, 217, 219, 221, 224, 226, 227, 228, 231, 233, 239, 242, 249 for selectively receiving, storing, and providing data in response to actions by the at least one user 112, 114, 116, 118, an analysis means 300 for analyzing data, a communication means 110 for sending and receiving data to and from the at least one user 112, 114, 116, 118 and programmed for controlling the functions performed by each of the representation means 148, 150, interface means 200, analysis means 300, communication means 110, and a storage means 132, 134, 136, 138, 140 for storing data saved by the at least one user 112, 114, 116, 118. The data includes information associated with at least one of the at least one patient 112 and at least one chronic illness, and at least one of the representation means 148, 150, interface means 200, analysis means 300, and communication means 110 is operatively associated with the at least one user 112, 114, 116, 118 through a network 144, 146. The data includes at least one decision support algorithm 300 for generating at least one care decision for the at least one patient 112 at the point of care and at least one visual representation 201, 204, 208, 214, 225, 232, 235, 237, 240, 243, 246 of the clinical health condition of the at least one patient 112. The interactive user controls 202, 205, 206, 209, 210, 211, 215, 216, 217, 219, 221, 224, 226, 227, 228, 231, 233, 239, 242, 249 are graphical user interface controls displayed on at least one of a user computer 150 or a mobile electronic device 148. At least one visual representation 201, 204, 208, 214, 225, 232, 235, 237, 240, 243, 246 is generated by the representation means 148, 150 and includes at least one of graphs 223, 230, 234 and charts 222, 229, 236, 241 associated with the clinical health condition of the at least one patient 112, and is displayed on at least one of a user computer 150 or a mobile electronic device 148.

In one embodiment, the system further includes an access control means 205-207 for controlling access to at least one of the representation means 148, 150, interface means 200, analysis means 300, communication means 110, and storage means 132, 134, 136, 138, 140, based upon the identity of the at least one user 112, 114, 116, 118 as a medical professional 116, health coach 114, patient 112, or research professional 118. The network 144, 146 is the internet 144 or a mobile electronic device network 146 and at least one of the representation means 148, 150, interface means 200, analysis means 300, and communication means 110 is operatively associated with at least one of a user computer 150 or user mobile electronic device 148 through the network 144, 146, where at least one of the representation means 148, 150, interface means 200, analysis means 300, and communication means 110 includes a web-based application.

In yet another aspect, the present invention relates to a method of using a computerized system 100 programmed for providing care support to at least one patient 112 having at least one chronic illness. In one embodiment, the method includes the steps of accessing the computerized system 100 through a network 144, 146 and providing identification designating that the user is a medical professional 116, health coach 114, patient 112, or research professional 118. The method also includes performing at least one of the steps of providing data including at least one of information from electronic medical records associated with the at least one patient 112, information associated with at least one treatment compliance program for treating the at least one chronic illness, and information associated with the clinical health condition of the at least one patient 112, receiving data including at least one decision support algorithm 300 for generating at least one care decision for the at least one patient 112 at the point of care, where the at least one decision support algorithm 300 includes at least one of disease-specific national diagnostic guidelines, disease-specific national treatment guidelines, patient-specific medication plans, and clinical care pathways, receiving an alert when a proposed medication or proposed medication dosage conflicts with a current medication or current medication dosage associated with the at least one patient 112, receiving data for supporting patient treatment compliance to chronic illness-specific treatment guidelines selected by at least one of the at least one medical professional 116 and the at least one health coach 114, providing data through the network 144, 146 from at least one of a health monitoring device 152, 154, 156, 158, mobile electronic device 148, and user computer 150, tracking use of patient-specific curriculum 238, 241, 244, 247 by the at least one patient 112, tracking communication between each of the at least one patient 112 and at least one of another patient 112, the medical professional 116, and the health coach 114, generating cost-benefit information associated with at least one treatment decision selected by at least one of the at least one medical professional 116 and at least one health coach 114, analyzing patient-specific data, and, receiving data associated with at least one clinical health trial.

In yet another aspect, the present invention relates to a method of using a computerized system 100 programmed for providing care support to at least one patient 112 having at least one chronic illness. In one embodiment, the method includes the steps of accessing the computerized system 100 through a network 144, 146 and providing identification designating that the user is a medical professional 116. The method also includes performing at least one of the steps of providing data that includes at least one of information from electronic medical records associated with the at least one patient 112, information associated with at least one treatment compliance program for treating the at least one chronic illness, and information associated with the clinical health condition of the at least one patient 112, receiving data that includes at least one decision support algorithm 300 adapted for generating at least one care decision for the at least one patient 112 at the point of care, where the at least one decision support algorithm 300 includes at least one of disease-specific national diagnostic guidelines, disease-specific national treatment guidelines, patient-specific medication plans, and clinical care pathways, and, receiving an alert when a proposed medication or proposed medication dosage conflicts with a current medication or current medication dosage associated with the at least one patient 112. In one embodiment, the method further includes the step of generating at least one care decision for the at least one patient 112 at the point of care.

In yet another aspect, the present invention relates to a method of using a computerized system 100 programmed for providing care support to at least one patient 112 having at least one chronic illness. In one embodiment, the method includes the steps of accessing the computerized system 100 through a network connection 144, 146 and providing identification designating that the user is a health coach 114. The method further includes performing at least one of the steps of receiving data for supporting patient treatment compliance to chronic illness-specific treatment guidelines selected by at least one of the medical professional 116 and health coach 114, tracking use of patient-specific curriculum 238, 241, 244, 247 by the at least one patient 112, and, tracking communication between each of the at least one patient 112 and at least one of another patient 112, the at least one medical professional 116, and the at least one health coach 114. In one embodiment, the method further includes the step of generating at least one decision associated with patient treatment compliance for the at least one patient 112.

In yet another aspect, the present invention relates to a method for using a computerized system 100 programmed for providing care support for at least one patient 112 having at least one chronic illness. In one embodiment, the method includes the steps of accessing the computerized system 100 through a network 144, 146 and providing identification designating that the user 112, 114, 116, 118 is the at least one patient 112. The method also includes performing at least one of the steps of providing data associated with the clinical health condition of the at least one patient 112 through the network 144, 146 from at least one of a health monitoring device 152, 154, 156, 158, mobile electronic device 148, and user computer 150, viewing at least one visual representation 201, 204, 208, 214, 225, 232, 235, 237, 240, 243, 246 of the clinical health condition of the at least one patient 112, viewing patient-specific curriculum 238, 241, 244, 247, and, communicating with at least one of another patient 112, the at least one medical professional 116, and the at least one health coach 114 through the network 144, 146. In one embodiment, the method further includes at least one of the steps of receiving, generating, and sending at least one of an SMS text message, electronic mail message, and social networking message, where the step of communicating with at least one of another patient 112, the at least one medical professional 116, and the at least one health coach 114 utilizes the network connection 144, 146.

In yet another aspect, the present invention relates to a method for using a computerized system 100 programmed for providing care support to at least one patient 112 having at least one chronic illness, where the system 100 includes a medical professional module 126 adapted for receiving, storing, and providing data in communication with at least one medical professional 116, a health coach module 124 adapted for receiving, storing, and providing data in communication with the at least one patient 112 and at least one health coach 114, a patient module 122 adapted for receiving, storing, and providing data in communication with the at least one patient 112, and a public health module 128 adapted for receiving, storing, and providing data in communication with at least one research professional 118, and where each of the medical professional module 126, health coach module 124, patient module, and public health module 128 is operatively associated with the corresponding at least one medical professional 116, at least one health coach 114, at least one patient 112 and at least one research professional 118 through a network connection 144, 146. In one embodiment, the method includes at least one of the steps of causing the medical professional module 126 to perform at least one of the functions of receiving data, storing data, and providing data, causing the health coach module 124 to perform at least one of the functions of receiving data, storing data, and providing data, causing the patient module 122 to perform at least one of receiving data, storing data, and providing data, and, causing the public health module 128 to perform at least one of receiving data, storing data, and providing data, where the data includes at least one decision support algorithm 300 for generating at least one care decision for the at least one patient 112 at the point of care and at least one visual representation 201, 204, 208, 214, 225, 232, 235, 237, 240, 243, 246 of the clinical health condition of the at least one patient 112.

In yet another aspect, the present invention relates to a method for using a computerized system 100 that is programmed for providing care support to at least one patient 112 having at least one chronic illness, where the system 100 includes a representation means 148, 150 for generating at least one visual representation 201, 204, 208, 214, 225, 232, 235, 237, 240, 243, 246 of data to at least one user 112, 114, 116, 118, and where the at least one user 112, 114, 116, 118 is a medical professional 116, health coach 114, patient 112, or research professional 118. The computerized system also includes an interface means 200 having interactive user controls 202, 205, 206, 209, 210, 211, 215, 216, 217, 219, 221, 224, 226, 227, 228, 231, 233, 239, 242, 249 for manipulating data in response to an action by the at least one user 112, 114, 116, 118, an analysis means 300 for analyzing data, a communication means 110 for sending and receiving data to and from the at least one user 112, 114, 116, 118, a storage means 132, 134, 136, 138, 140 for storing data saved by the at least one user, and a network server 110 in communication with and programmed for controlling the functions performed by each of the representation means 148, 150, interface means 200, analysis means 300, communication means 110, and storage means 132, 134, 136, 138, 140. At least one of the representation means 148, 150, interface means 200, analysis means 300, and communication means 110 is operatively associated with the at least one user 112, 114, 116, 118 through a network 144, 146. In one embodiment, the method includes at least one of the steps of causing the representation means 148, 150 to generate at least one visual representation 201, 204, 208, 214, 225, 232, 235, 237, 240, 243, 246 of data, causing the interactive user controls 202, 205, 206, 209, 210, 211, 215, 216, 217, 219, 221, 224, 226, 227, 228, 231, 233, 239, 242, 249 of the interface means 200 to selectively receive, store, and provide data, causing the analysis means 300 to analyze data, causing the communication means 110 to send and receive data, and, causing the network server 110 to communicate with at least one of the representation means 148, 150, interface means 200, analysis means 300, communication means 110, and storage means 132, 134, 136, 138, 140, and to control each function of the representation means 148, 150, interface means 200, analysis means 300, communication means 110, and storage means 132, 134, 136, 138, 140. The data includes information associated with at least one of the at least one patient 112 and at least one chronic illness.

In yet another aspect, the present invention relates to software stored on a computer-readable medium for causing a computing system to perform functions for interacting with at least one user 112, 114, 116, 118 of a system 100, where the system 100 is programmed for providing care support to at least one patient 112 having at least one chronic illness. In one embodiment, the functions include receiving, storing, and providing data in communication with at least one medical professional 116, receiving, storing, and providing data in communication with at least one health coach 114, receiving, storing, and providing data in communication with at least one patient 112, and, receiving, storing, and providing data in communication with at least one research professional 118. The data includes at least one decision support algorithm 300 for generating at least one care decision for the at least one patient 112 at the point of care and at least one visual representation 201, 204, 208, 214, 225, 232, 235, 237, 240, 243, 246 of the clinical health condition of the at least one patient 112.

In yet another aspect, the present invention relates to software stored on a computer-readable medium for causing a computing system to perform functions for interacting with at least one user 112, 114, 116, 118 of a system 100 programmed for providing care support to at least one patient 112 having at least one chronic illness. In one embodiment, the functions include generating at least one visual representation 201, 204, 208, 214, 225, 232, 235, 237, 240, 243, 246 of data to the at least one user 112, 114, 116, 118, selectively receiving, storing, and providing data in response to an action by the at least one user 112, 114, 116, 118, analyzing data, sending data, and receiving data to and from the at least one user 112, 114, 116, 118, and, storing data saved by the at least one user 112, 114, 116, 118. The data includes information associated with at least one of the at least one patient 112 and at least one chronic illness, and the communication occurs through a network 144, 146.

Figure 1A:
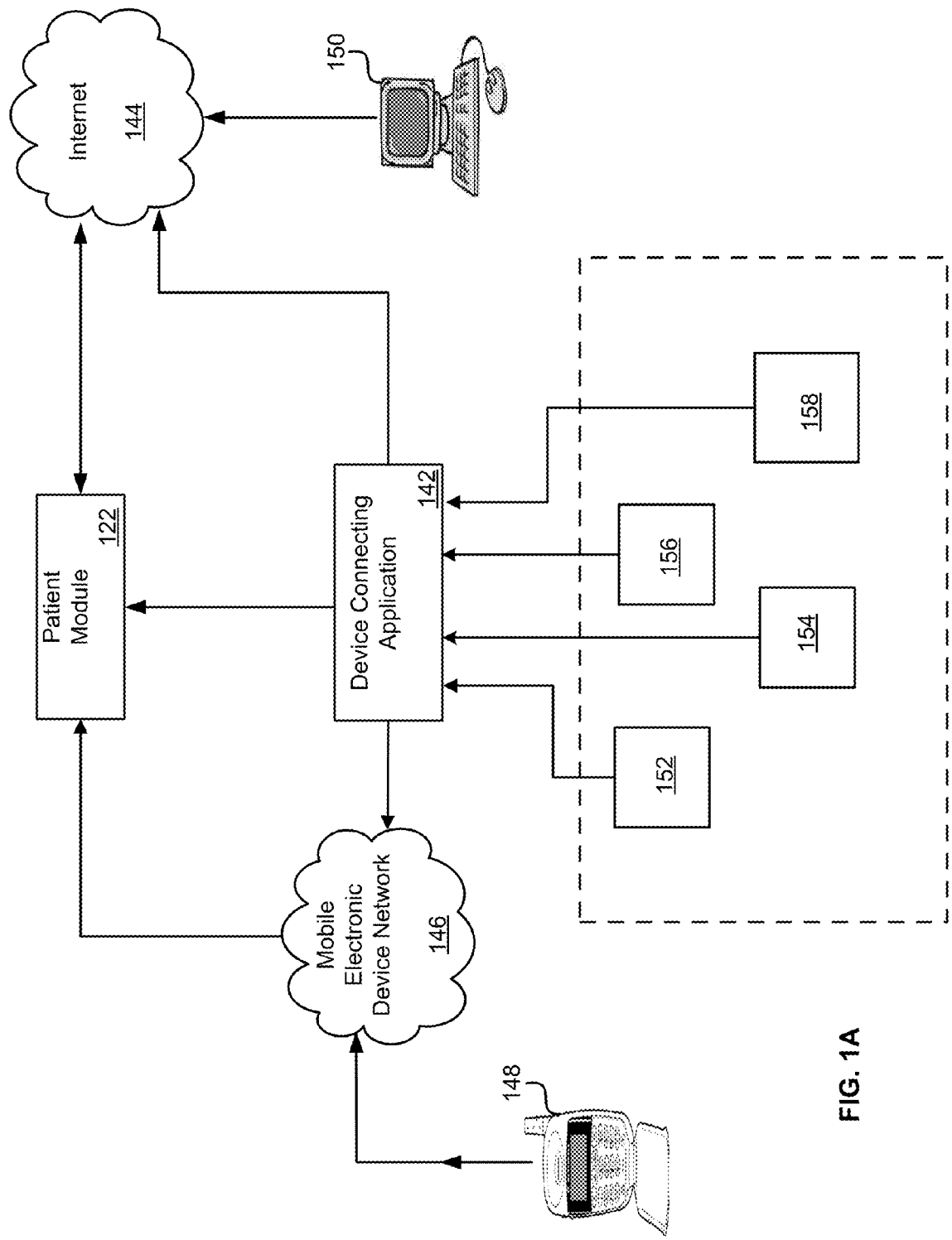
FIG. 1A shows schematically a further illustration of the patient module of the computerized system of FIG. 1, according to one embodiment of the present invention.

Now referring specifically to FIGS. 1 and 1A, FIG. 1 shows schematically a computerized system 100 programmed for providing care support to at least one patient 112 having at least one chronic illness, according to one embodiment of the present invention and the relationship between various users 112, 114, 116, 118, storage means 132, 134, 136, 138, 140 and a communication means 110 for the computerized system 100. In operation, from a high level design standpoint, the system 100 enables close monitoring of the health of a patient and access is through multiple devices, such as a computer, cell phone, or health monitoring device. Easy communication is also allowed between patients and physicians, and early detection potential is provided for detecting deteriorating conditions, by physician intervention. Treatment compliance and adherence is promoted, and dynamically linked disease specifics curriculum is provided, including quizzes and rewards programs. Behavior modification is also allowed through social networking, as is the ability to health forecast by research scientists and/or epidemiologists.

The system 100 can be a web-based application such as a publically available or proprietary web page, and includes a patient module 122, medical professional module 126, health coach module 124, and public health module 128 connected to the communication means 110, which here is a server 110 for a network. The users 112, 114, 116, 118 shown are a patient 112, health coach 114, medical professional 116, and a research professional 118. The patient 112 is a patient having at least one chronic illness, such as diabetes, heart disease, or asthma. The health coach 114 is a patient representative, also referred to as a health guide or care champion, that works with the patient 112 either remotely or directly at the point of care, such as a physicians office, in order to assist the patient 112 to make decisions regarding chronic illness care and to assist the patient 112 in selecting and adhering to treatment compliance programs and lifestyle changes or nutritional changes, for example. The medical professional 116 can be a physician, physician assistant, nurse practitioner, or nurse, for example, who works with the patient 112 to treat the chronic illness directly at the point of care. The research professional 118 can be a public health researcher that works to recruit patients for clinical trials.

The patient module 122 is operatively associated with a patient 112, the health coach module 124 is operatively associated with a health coach 114, the public health module is operatively associated with a research professional 118, and the medical professional module 126 is operatively associated with a medical professional 116. As shown in this example, the storage means 140 is a public health/research database, the storage means 136 is a physicians EMR/PHR database, the storage means 138 is a public health database, the storage means 132 is a user management database, and the storage means 134 is a usage tracking and social networking database.

In operation, the patient module 122 can allow for a patient to upload health data by connecting health monitoring devices to internet enabled computers or cell phones, or by manually entering the data through a website. It can allow for a patient to own his or her data and it can give the patient access to a selected health coach or physician to view or update the data, where and the patient can revoke access anytime. Various color coded (red, yellow, green ranges) displays can be made, such as in the form of views of data in charts and tables. The patient module 122 can also suggest action to the patients based on data. It further can allow for tracking of curriculum usage data for patient reward programs, such as on successful completion of curriculum modules. The patient module 122 also can encourage and track social networking, such as through email, or text messaging from the system website between patients and physicians or health coaches, thereby helping in positive behavior modification, such as through lifestyle changes, diet, or exercise.

Each of the medical professional module 126 and health coach module 124, in operation, allows for a medical professional to have the EMR connected to the system to enable data exchange. A medical professional can also use the medical professional module store intelligent algorithms on the system for patient treatment compliance. Further, a medical professional and a health coach can communicate with a patient through the system, such as through a system website, by the use of a computer or cell phone. The public health module 128, in operation, can allow for research professionals to use a public health research data repository to do statistical analysis and forecasts, or to recruit patients for clinical trials.

FIG. 1A shows schematically a further illustration of the patient module 122 of the computerized system 100 of FIG. 1, according to one embodiment of the present invention. As shown, the patient module 122 is operatively associated with device connecting application 142, which receives and can also provide data to and from one or more health monitoring devices 152, 154, 156, 158 used by the patient 112, such as connected to a user computer 150. The device connecting application 142 can connect with the patient module 122 either directly, such as at the point of care, or through a network connection such as the internet 144. Data can be received and provided by the patient 122 in connection with the patient module 122 either remotely, such as through a user computer 150 connected to the internet 144, or a mobile electronic device 148 such as a cell phone or PDA that is connected through a mobile electronic device network 146, such as a wireless cell phone network. The device connecting application 142 can also communicate with the patient module 122 through the mobile electronic device network 146.

Figure 2A:
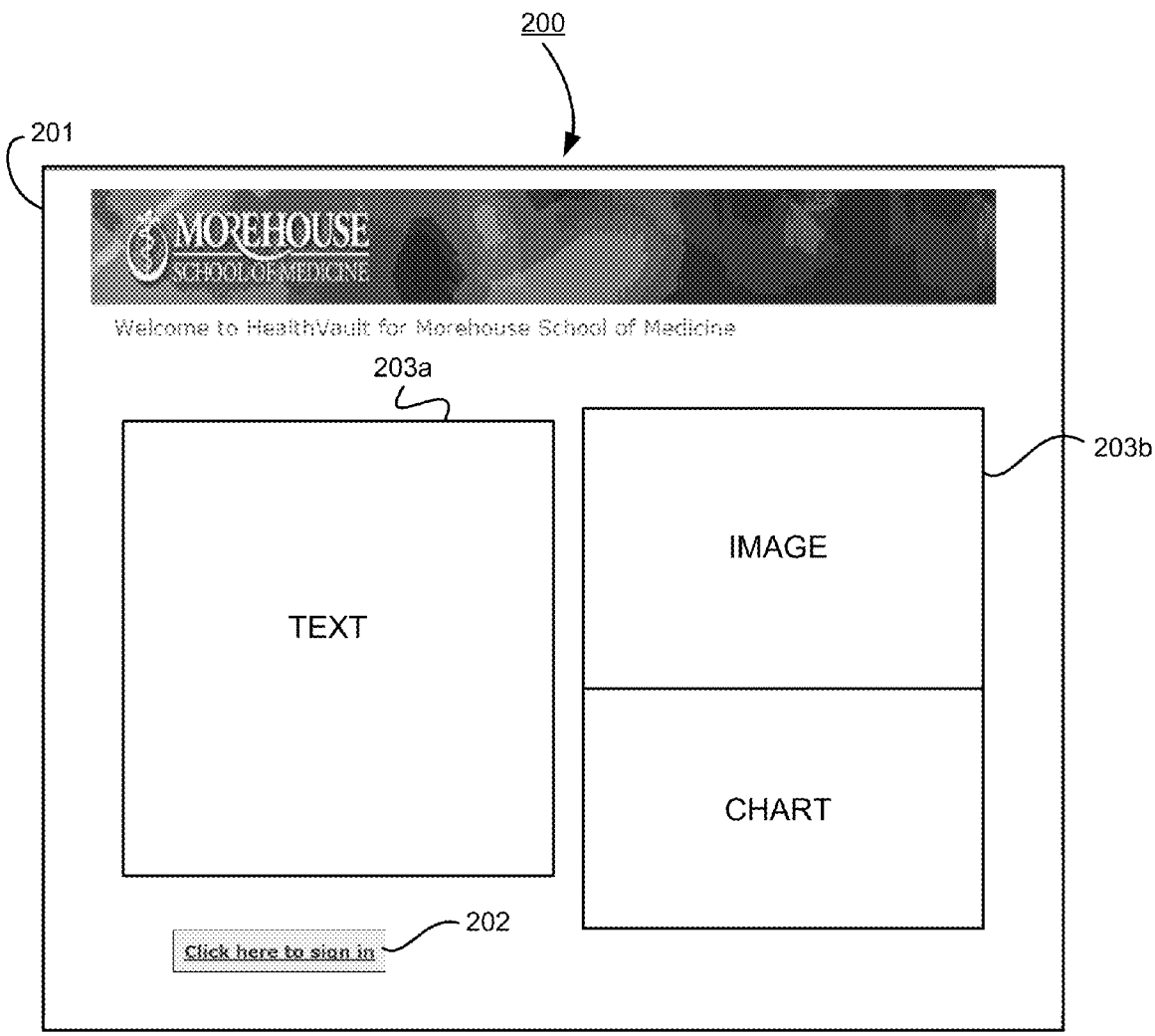
FIG. 2A shows schematically an interface means for using the computerized system of FIGS. 1 and 1A, according to one embodiment of the present invention.
Figure 2B:
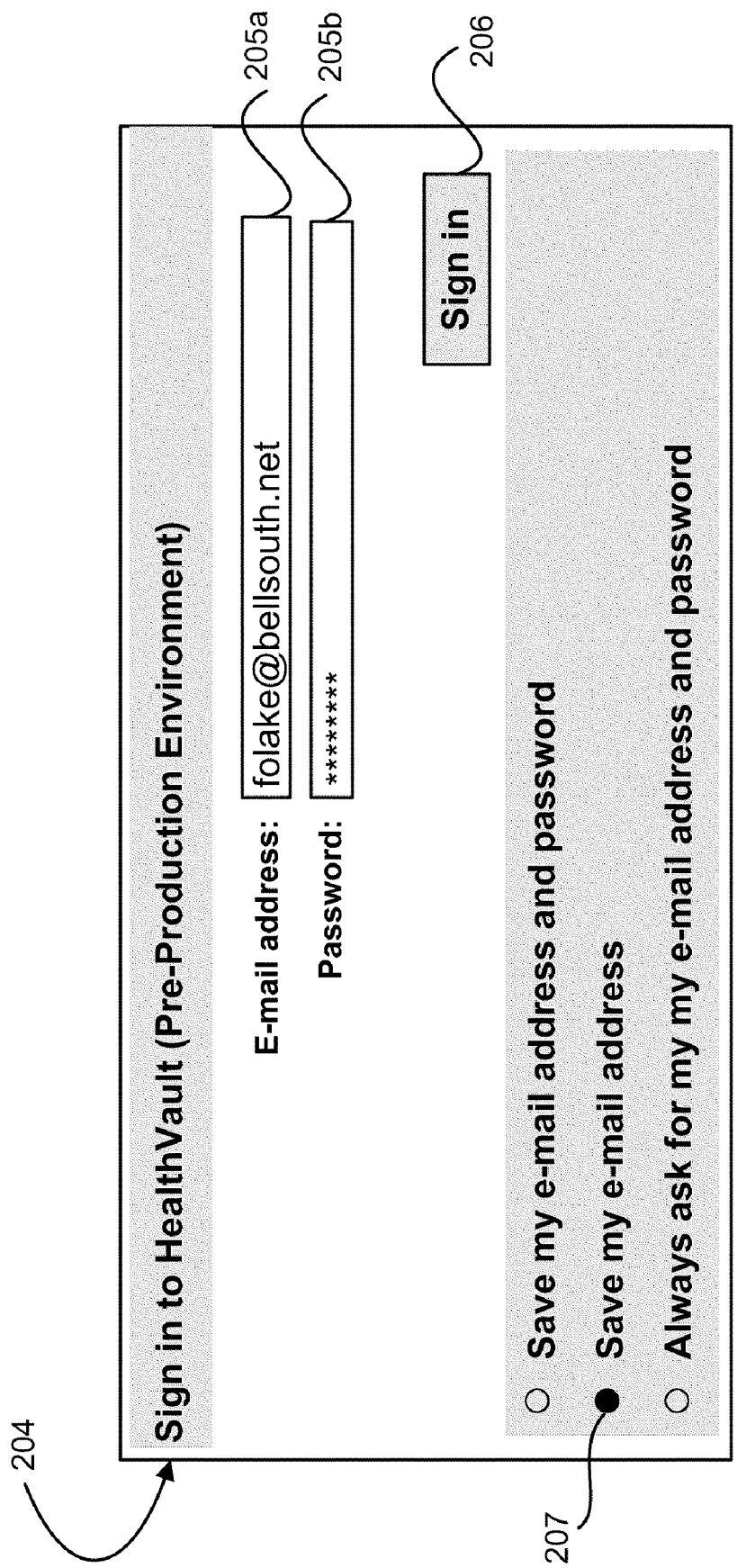
FIG. 2B shows schematically a further illustration of the interface means shown in FIG. 2A, according to one embodiment of the present invention.
Figure 2C:
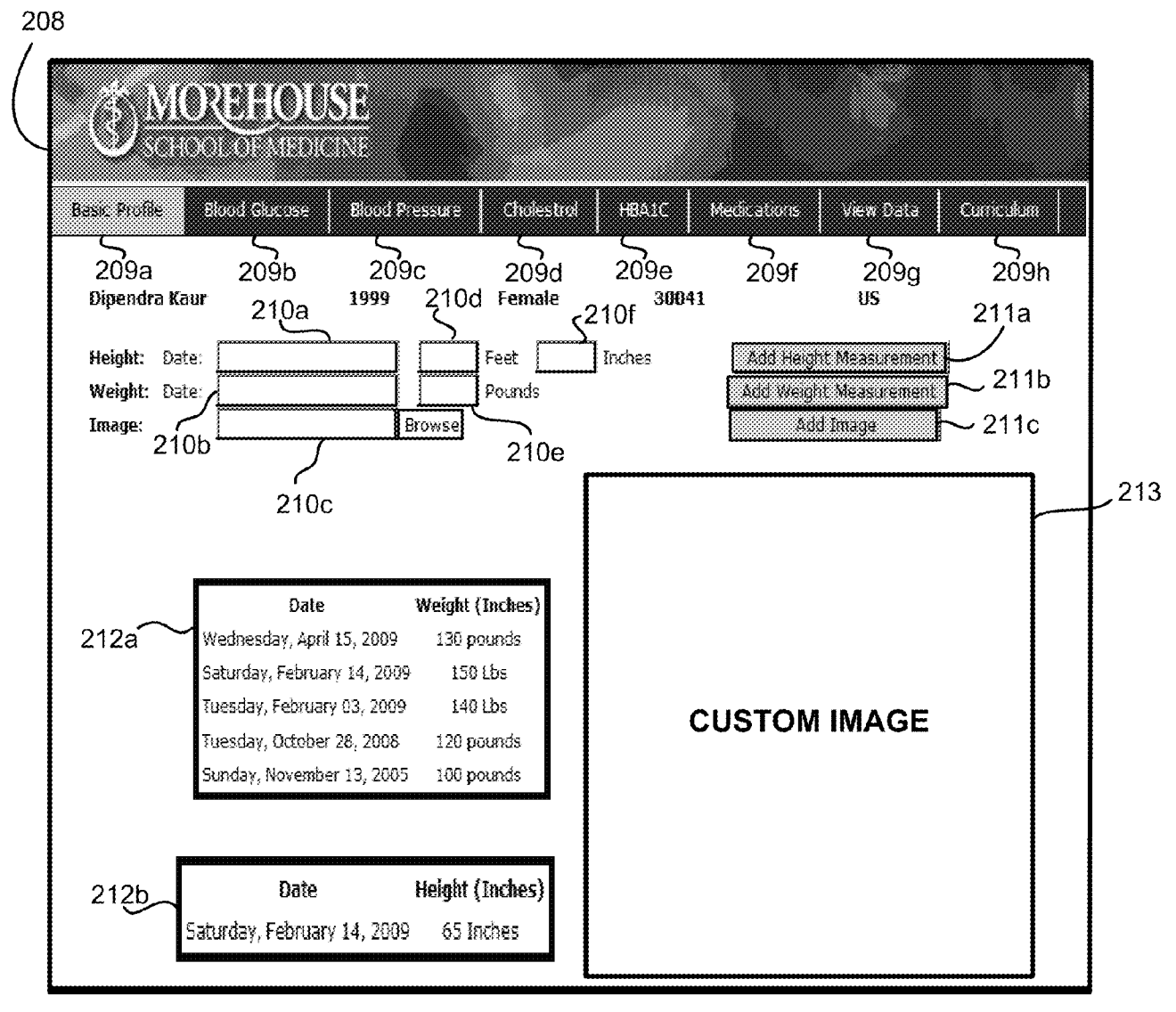

FIGS. 2A-2M show schematically an interface means 200 for using the computerized system 100 of FIGS. 1A and 1B, according to one embodiment of the present invention. FIG. 2A shows schematically an interface means 200 for using the computerized system 100 of FIGS. 1 and 1A, according to one embodiment of the present invention. As shown in FIG. 2A, in the main page 201 used to provide access to the system 100, which can be an internet home page running on a webbrowser, the interface means 200 is a graphical user interface such as a WINDOWS® operating system with controls 202 such as active web links. Also shown in FIG. 2A is a visual representation 203 of data, showing a table of patient health condition data, as well as a color-coded chart. FIG. 2B shows schematically a further illustration of the interface means 200 shown in FIG. 2A, according to one embodiment of the present invention. Here, an access control means 204 is shown, which includes controls 205a, 205b, 206, and 207. FIG. 2C shows schematically a further illustration of the interface means 200 shown in FIGS. 2A and 2B, according to one embodiment of the present invention. Here, a graphical interface 208 is shown, where basic profile information and other information associated with the clinical health condition of the patient 112 can be entered by the user 112, 114, 116, 118, using controls 210a-f and 211a-c. As shown, controls 209a-h are graphical user interface tabs, for taking the user to each page of the graphical user interface for performing various functions of the system 100. As shown, the controls 210a-f are input boxes for entering data, and the controls 211a-c are click buttons for performing additions of various clinical data associated with the patient 112. Also shown are visual representations 212a, 212b of patient data in the form of charts and numeric representations. A visual representation 213 is shown of an image that can be selectively associated with the patient, such as a custom image corresponding to health condition or preferences, using control 211c.

Figure 2E:
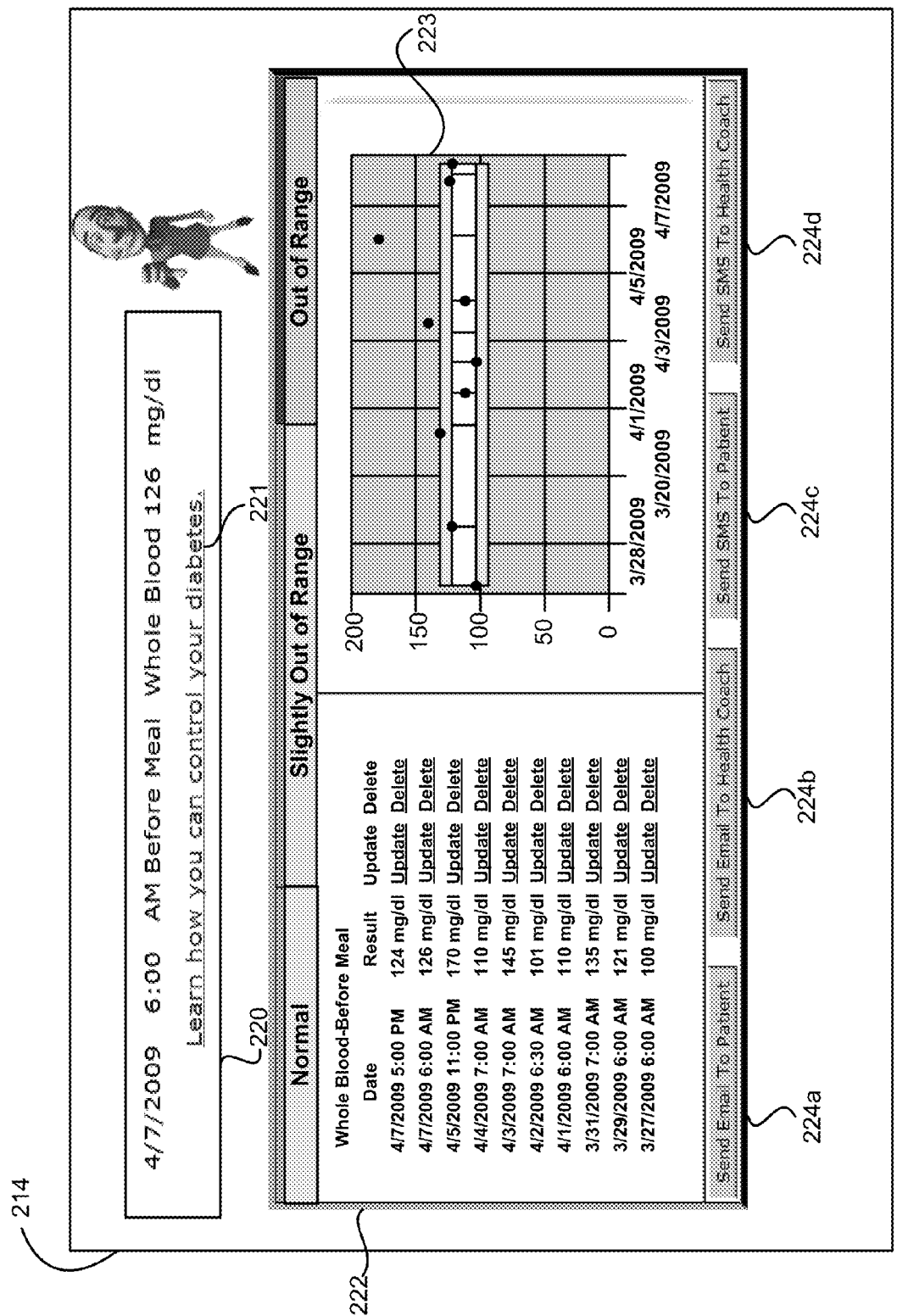
FIG. 2E shows schematically a further illustration of the interface means shown in FIGS. 2A-2D, according to one embodiment of the present invention.

FIG. 2D shows schematically a further illustration of the interface means 200 shown in FIGS. 2A-2C, according to one embodiment of the present invention, where the graphical user interface 214 shown here corresponds to patient blood glucose, and data associated with the patient blood glucose can be entered using the controls 216, 217, and 219. Also shown in FIG. 2D are visual representations 215 and 218, which are numeric representations of data and images associated with using a glucometer, respectively. FIG. 2E shows schematically a further illustration of the interface means 200 shown in FIGS. 2A-2D, according to one embodiment of the present invention, which is a continuation from the top of the same graphical user interface page 214 shown in FIG. 2D. Visual representations 220, 222, and 223 of patient-related data are also shown. Controls 224a-224d allow for a user to send an email message or SMS text message to the patient 112 or health coach 114.

Figure 2F:
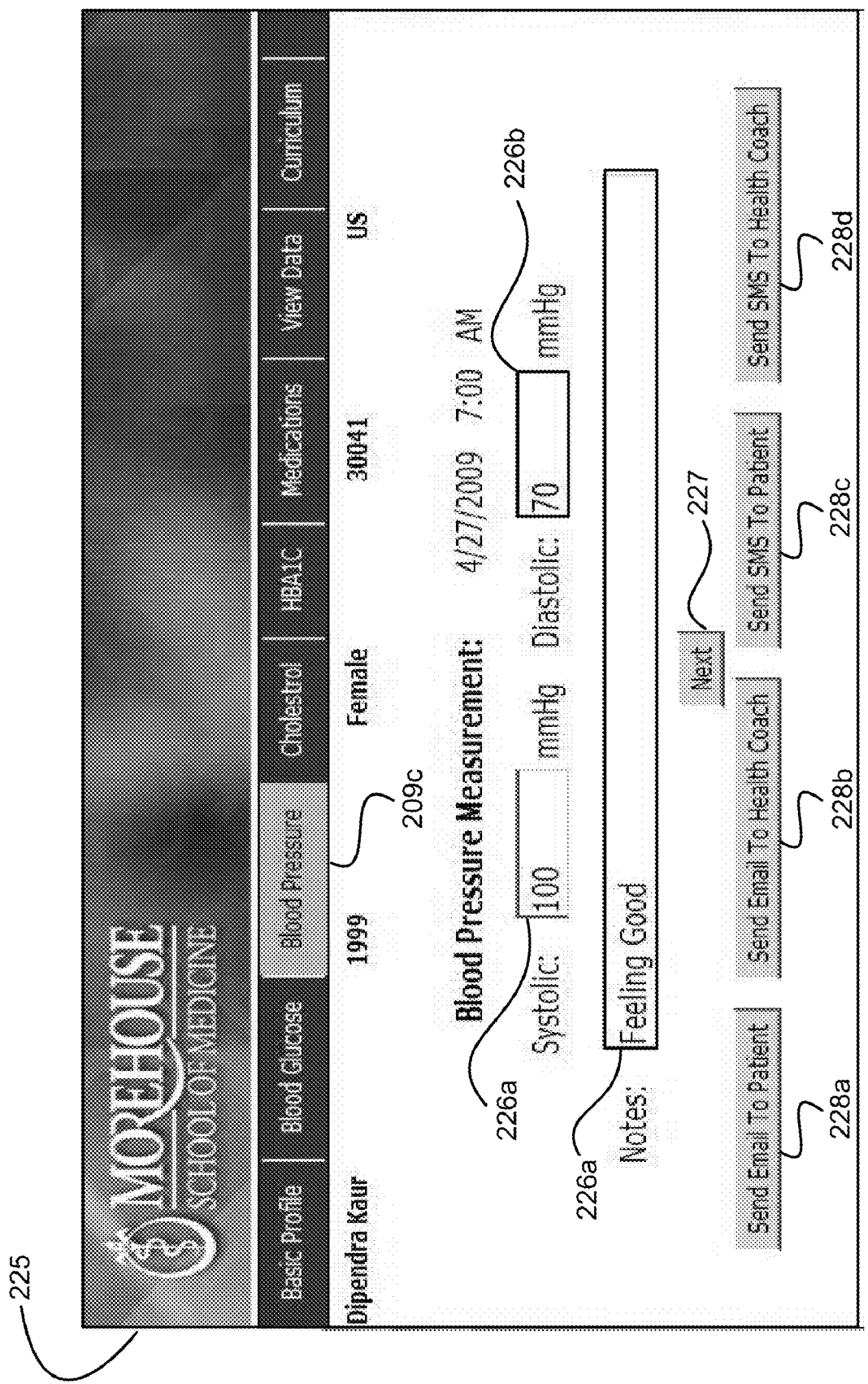
FIG. 2F shows schematically a further illustration of the interface means shown in FIGS. 2A-2E, according to one embodiment of the present invention.
Figure 2G:
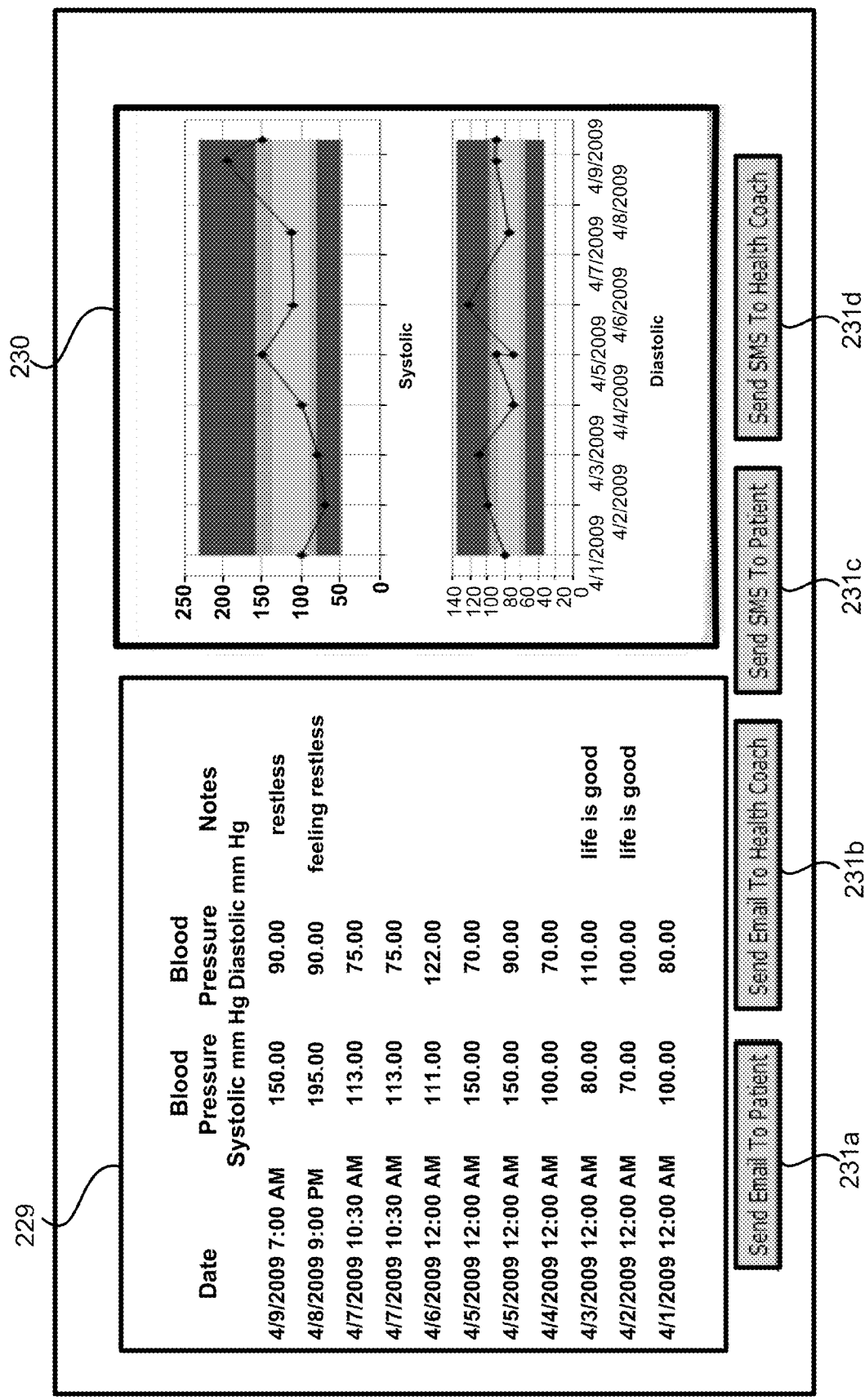
FIG. 2G shows schematically a further illustration of the interface means shown in FIGS. 2A-2F, according to one embodiment of the present invention.
Figure 2H:
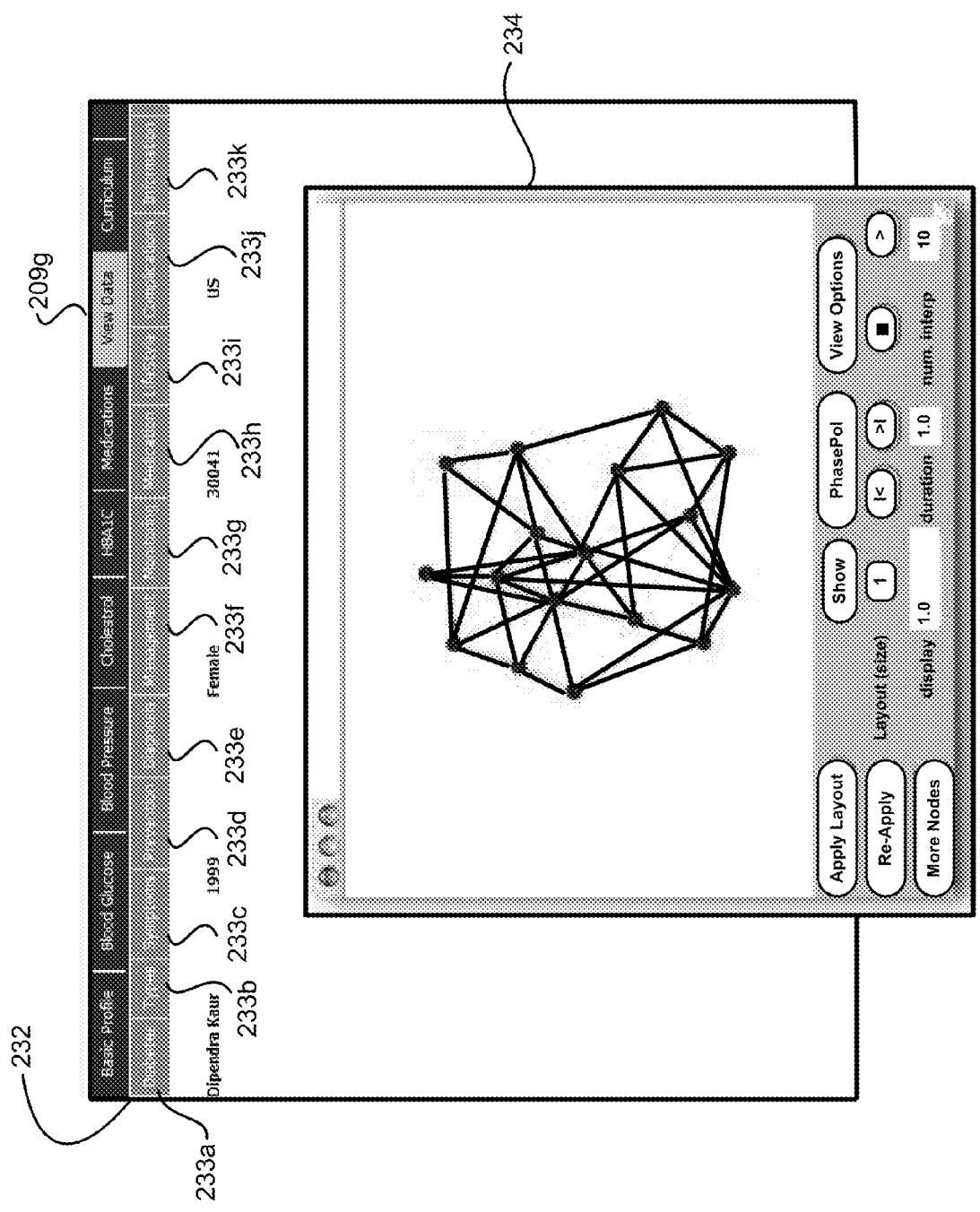
FIG. 2H shows schematically a further illustration of the interface means shown in FIGS. 2A-2G, according to one embodiment of the present invention.
Figure 2J:
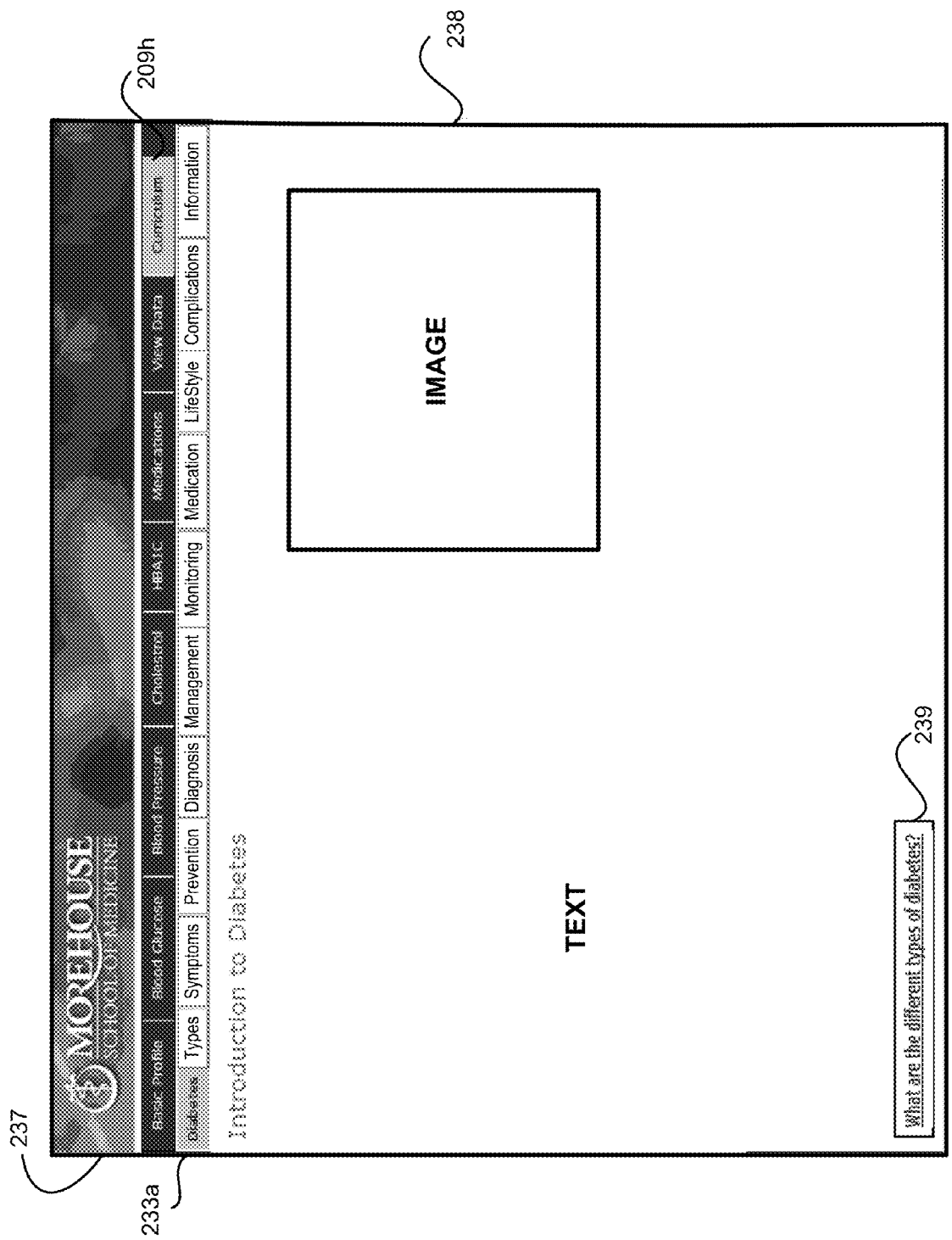
FIG. 2J shows schematically a further illustration of the interface means shown in FIGS. 2A-2I, according to one embodiment of the present invention.

FIG. 2F shows schematically a further illustration of the interface means 200 shown in FIGS. 2A-2E, according to one embodiment of the present invention. In FIG. 2F, the graphical user interface 225 here corresponds to patient blood pressure, and controls 226a-c, 227, and 228a-d are shown for performing various functions selected by the user 112, 114, 116, 118, such as entering data and sending messages to other users. In FIG. 2G, which is a continuation of the graphical user interface screen shown in FIG. 2F, visual representations 229 of data are shown, as are controls 231a-d for sending messages to users 112, 114, 116, 118. FIG. 2H shows schematically a further illustration of the interface means 200 shown in FIGS. 2A-2G, according to one embodiment of the present invention, where the graphical user interface 232 here has further controls in the forms of tab 233a-233k for performing detailed functions under the main category of viewing data, as indicated by tab 209g. A pop-up type window 234 is also shown, which is a visual representation of social networking activity such as communication being made between users, such as between patients and other patients, or between patients and physicians or health coaches. FIG. 2I shows schematically a further illustration of the interface means 200 shown in FIGS. 2A-2H, according to one embodiment of the present invention, where the graphical user interface 235 here also corresponds to viewing data, as in FIG. 2H, and a visual representation in table form of patient usage of curriculum such as educational information, quizzes, or rewards programs associated with the chronic illness of the patient. FIG. 2J shows schematically a further illustration of the interface means 200 shown in FIGS. 2A-2I, according to one embodiment of the present invention, where this representation 237 corresponds to curriculum to be used or viewed by the patient, including information about chronic illness 238a and video displays 238b associated with chronic illness. Also shown is a control 239 in the form of an active link for accessing further curriculum information.

Figure 2L:
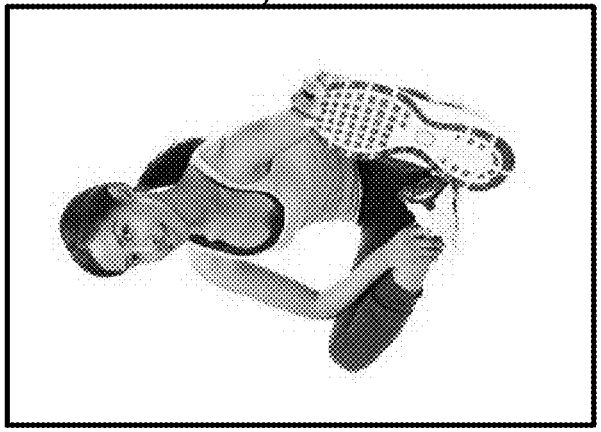
FIG. 2L shows schematically a further illustration of the interface means shown in FIGS. 2A-2K, according to one embodiment of the present invention.
Figure 2M:
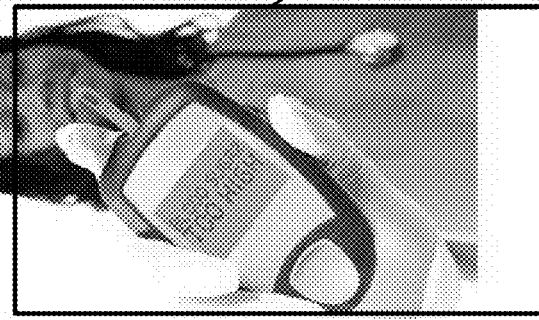
FIG. 2M shows schematically a further illustration of the interface means shown in FIGS. 2A-2L, according to one embodiment of the present invention.

FIG. 2K shows schematically a further illustration of the interface means 200 shown in FIGS. 2A-2J, according to one embodiment of the present invention, where the graphical user interface representation 240 here again corresponds to patient curriculum. Here, educational information in the form of a chart 241 is shown, as is a control 242 button for moving to more curriculum associated with the patient 112 and chronic illness. FIG. 2L shows schematically a further illustration of the interface means 200 shown in FIGS. 2A-2K, according to one embodiment of the present invention, where here the graphical user interface 243 is again associated with curriculum, and more specifically lifestyle, as indicated by tabs 209h and 233i, and visual representations 244 and 245 are also shown. FIG. 2M shows schematically a further illustration of the interface means 200 shown in FIGS. 2A-2L, according to one embodiment of the present invention, where the user graphical interface representation 246 here corresponds to patient curriculum 209h and more specifically diagnosis, as indicated by tabs 209h and 233e. Also shown are visual representations 247, 248 of curriculum associated with chronic illness, as is a control 249.

Figure 3A:
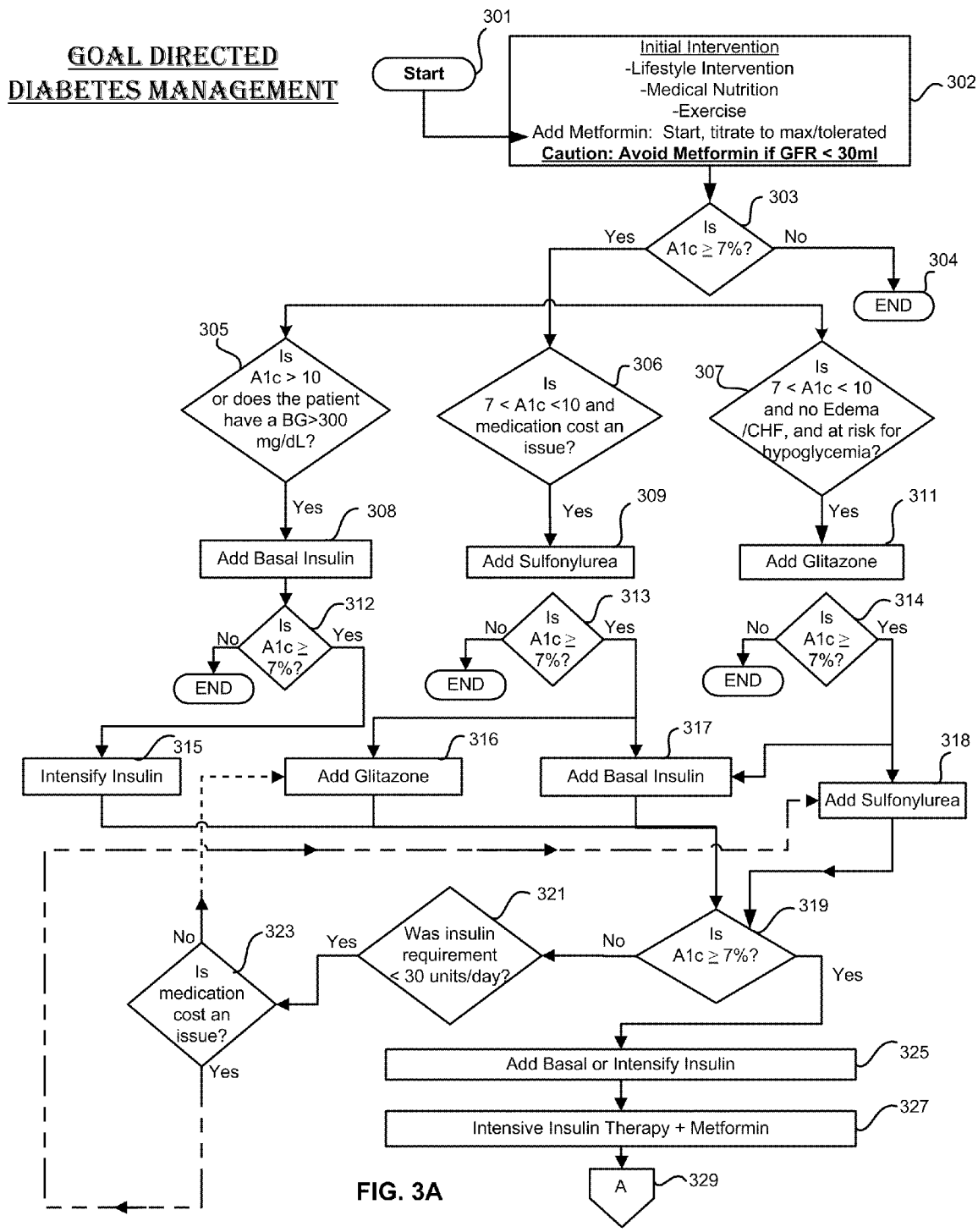
FIG. 3A shows a flow chart illustrating the steps performed by an analysis means, according to one embodiment of the present invention.
Figure 3B:
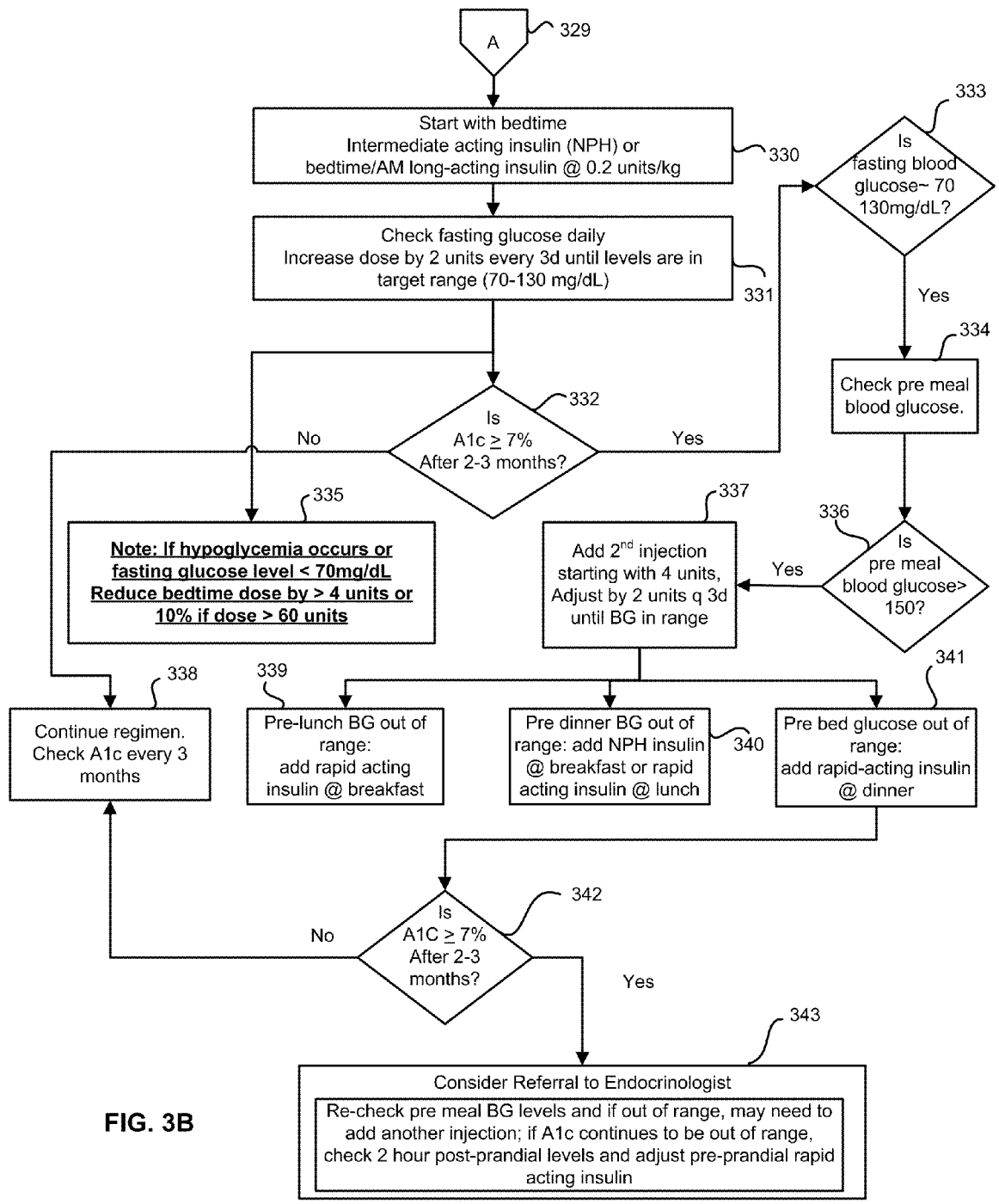
FIG. 3B shows a flow chart illustrating further steps of the method as shown in the flow chart of FIG. 3A, according to one embodiment of the present invention.

FIG. 3A shows a flow chart illustrating the steps performed by an analysis means 300, according to one embodiment of the present invention, and FIG. 3B shows a flow chart illustrating further steps of the method as shown in the flow chart of FIG. 3A, according to one embodiment of the present invention. The analysis means 300 as shown in this embodiment is a decision support algorithm used for goal directed management of diabetes. At step 301, a medical professional, for example, medical professional 116 as shown in FIG. 1A using the medical professional module 126, through the interface means 200 shown in FIGS. 2A-2L and using, for example, a user computer 150, begins use in a clinical setting at the point of care for at least one patient, such as patient 112 shown in FIG. 1A. An initial intervention with the patient occurs at step 302, which can include lifestyle intervention, medical nutrition, exercise, and also medication, where here the medication added is Metformin titrated to a maximum and/or tolerated dosage. The algorithm 300 at this step 302 also notifies the medical professional that Metformin should be avoided where the patient GFR is less than a certain level, here 30 ml. Such a notification can be in the form of a visual prompt displayed as a visual representation to the medical professional, or an alarm such as in the form of an audio alert. Also, the notification can be in one of many various levels of obligation with regard to the medical professional actually implementing the step or steps set forth in the notification, for example, from the level of a helpful note or suggestion up to the level of a mandate or required action to be taken by the medical professional before another step of the clinical encounter can take place. That is, the analysis means is in this example a tool to support a decision that is ultimately made by the medical professional in relation to the patient, meaning that useful information is provided at the setting of the clinical encounter. Also, as discussed above in connection with FIG. 1B, health monitoring devices 152-158 can be provided in communication with the interface means and generally the computerized system, such that data to and from such devices can be transformed, such as into settings or functions implemented by particular devices that are directly in contact with the health condition of the patient.

From the initial intervention step 302, flow continues to step 303, where it is determined if the patient has an A1c of greater than or equal to a certain level, here 7%. In order for this determination to be made, the medical professional can be prompted to enter the levels monitored directly at the point of care, using the interface means. The patient A1c is checked every 90 days, and in this example, the algorithm 300 operates to support decisions made by the medical professional to maintain target levels for a general patient at or below 7%. However, certain patients, such as those having high risk factors or other complicating considerations, for instance, may need to maintain a target level of less than or equal to 6.5%. Also, in this example the target fasting self-monitored blood glucose (SMBG) is less than or equal to 110 mg/ml, and the two-hour post-prandial (PP) target is less than or equal to 140-180 mg/dL. At step 303 if it is determined that the patient A1c is not greater than or equal to 7%, then operational flow ends, at step 304. At step 303 if the patient A1c is greater than or equal to 7%, then flow continues to one of three steps: 305, 306, or 307. If, at step 305 the patient A1c is greater than 10% or the patient has blood glucose greater than 300 mg/dL, then the medical professional is notified at step 308 that adding Basal insulin to the patient medication is most effective, and that lifestyle intervention should start with the insulin, which should be titrated rapidly to return glucose to target levels. From this step 308, when the patient A1c is next checked, at step 312, if the level is still at or above 7%, then a notification is made to intensify insulin, at step 315. If, at step 306 the patient A1c is greater than 7% but less than 10%, and if cost of a particular medication is an issue to the patient, as determined for instance by the medical professional at the clinical encounter, then the medical professional is notified at step 309 that a relatively inexpensive medication such as Sulfonylurea is to be added to the patient medication, that is, to the Metformin added at step 302, where the patient GFR is not less than 30 ml. When the patient A1c is next checked, at step 313, if the level is still greater than 7%, then a notification is made to either add Glitazone or add basal insulin, at steps 316 and 317, respectively. If, at step 307 the patient A1c is greater than 7% and less than 10% and there is no edema or congestive heart failure, and the patient is at risk for hypoglycemia, then a notification is made that Glitazone can be added to the existing medication, at step 311. When the patient A1C is next checked, at step 314, then if the level is still greater than 7% and the same existing conditions apply, then a notification is made to add basal insulin or add Sulfonylurea, at steps 317 and 318, respectively. After each of these possible steps 315, 316, 317, and 318, another A1C determination is made, at step 319. If at this step it is determined that the patient A1C is greater than 7%, then a notification is made to add basal insulin or intensify the existing insulin regimen, insulin, at step 325, followed by intensive insulin therapy and the Metformin, at step 327. From this step, flow proceeds to step 329 and continues to FIG. 3B, which shows the operational flow for intensive insulin therapy. However, if at step 319 it is determined that the patient A1C is not greater than or equal to 7%, and it is determined at step 321 that the insulin requirement was less than 30 units/day, then another determination is made as to whether medication cost is an issue to the patient, at step 323. If cost is an issue, then flow moves to step 318, where a notification is made to add Sulfonylurea. However, if cost is not an issue at step 323, then a notification is made to add Glitazone, at step 316.

Now referring specifically to FIG. 3B, at step 330, notification is made to start with bedtime intermediate acting insulin (NPH) or bedtime/AM long-acting insulin at 0.2 units/kg, followed by, at step 331, notification to check fasting glucose daily and increase dose by two units every three days until levels are in a target range, for example, 70-130 mg/dL. Notification is made at step 335 that if hypoglycemia occurs or fasting glucose level is less than 70 mg/dL, then the bedtime dose is to be reduced by greater than four units or 10% if the dose is greater than 60 units. A determination is made at step 332 if the patient A1c is greater than or equal to 7% after 2-3 months. If the patient A1c is not greater than or equal to 7% after 2-3 months, then a notification is made to continue the regimen and check A1c every three months, at step 338. However, if the patient A1c is greater than or equal to 7% at step 332, then operational flow of the decision support algorithm 300 moves to step 333, where a determination is made if fasting glucose is around 70-130 mg/dL. If so, then a notification is made to check pre meal blood glucose, at step 334. If it is determined at step 336 that the pre meal blood glucose is greater than 150 mg/dL, then a notification is made at step 337 to add a second injection starting with four units, with an adjustment made by two units per 3 days until the blood glucose is within a target range. From this step, operational flow moves to one of three steps: 339, 340, or 341. At step 339, if the pre-lunch blood glucose is out of range, then notification is made to add rapid acting insulin at breakfast, and flow continues to step 342. At step 340, if the pre-dinner blood glucose is out of range, then notification is made to add NPH insulin at breakfast or rapid acting insulin at lunch. At step 341, if the pre bedtime glucose is out of range, then notification is made to add rapid-acting insulin at dinner, and flow continues to step 342. If at step 342 it is determined that the patient A1c is greater than or equal to 7% after 2-3 months, then a notification is made for the medical professional to consider referring the patient to an endocrinologist, at step 343, and also at step 343, notification is made to re-check pre-meal blood glucose levels and if they are out of range, another injection may need to be added. Additionally, notification is made that if the patient A1c continues to be out of target range, then a check should be made of two hour post-prandial levels and to adjust pre-prandial rapid acting insulin. However, if at step 342 it is determined that the patient A1c is not greater than or equal to 7% after 2-3 months, then notification at step 338 is made to continue the regimen and check patient A1c every three months.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A computerized system programmed for providing care support to at least one patient having at least one chronic illness, comprising a server comprising:
   (a) a medical professional module adapted for receiving, storing, and providing data in communication with at least one medical professional at the point of care, wherein the medical professional module comprises at least one algorithm for generating at least one care decision for the at least one patient at the point of care, wherein the at least one algorithm is based at least in part on at least one of disease-specific national diagnostic guidelines, disease-specific national treatment guidelines, patient-specific medication plans, and clinical care pathways;
   (b) a health coach module adapted for receiving, storing, and providing data in communication with the at least one patient and at least one health coach;
   (c) a patient module adapted for receiving, storing, and providing data in communication with the at least one patient; and
   (d) a public health module adapted for receiving, storing, and providing data in communication with at least one research professional, wherein the public health module is adapted for generating cost-benefit information associated with at least one treatment decision for a chronic illness selected by at least one of the at least one medical professional and at least one health coach,
   wherein the server and each of the medical professional module, health coach module, patient module, and public health module are operatively associated with a corresponding one of the at least one medical professional, the at least one health coach, the at least one patient, and the at least one research professional through a network computing system to perform for interacting with at least one user of the system programmed for providing care support to at least one patient having at least one chronic illness.

2. The system of claim 1, wherein the system is further programmed for performing at least one of the acts of:
   (a) providing data comprising at least one of information from electronic medical records associated with the at least one patient, information associated with at least one treatment compliance program for treating the at least one chronic illness, and information associated with the clinical health condition of the at least one patient;
   (b) receiving an alert when a proposed medication or proposed medication dosage conflicts with a current medication or current medication dosage associated with the at least one patient;
   (c) receiving data for supporting patient treatment compliance to chronic illness-specific treatment guidelines selected by at least one of the at least one medical professional and the at least one health coach;
   (d) providing data through the network from at least one of a health monitoring device, mobile electronic device, and user computer;
   (e) tracking use of patient-specific curriculum by the at least one patient; (g) tracking communication between each of the at least one patient and at least one of another patient, the medical professional, and the health coach;
   (f) generating cost-benefit information associated with at least one treatment decision selected by at least one of the at least one medical professional and at least one health coach; (i) analyzing patient-specific data; and
   (g) receiving data associated with at least one clinical health trial.

3. The system of claim 1, wherein each of the medical professional module, health coach module, patient module, and public health module is further operatively associated with at least one data storage means through the network, wherein the at least one data storage means is adapted for storing data saved by the at least one corresponding medical professional, at least one health coach, at least one patient, and at least one research professional.

4. The system of claim 1, wherein the at least one chronic illness is heart disease, diabetes, or asthma.

5. The system of claim 1, wherein the network is at least one of the internet and a mobile electronic device network.

6. The system of claim 1, wherein the at least one medical professional is a physician, physician assistant, nurse, or nurse practitioner.

7. The system of claim 1, wherein the data received by at least one of the medical professional module and health coach module comprises at least one of information from electronic medical records associated with the at least one patient, information associated with treatment compliance programs for treating the at least one chronic illness, and information associated with the clinical health condition of the at least one patient.

8. The system of claim 1, wherein the medical professional module is further adapted for providing an alert to the at least one medical professional when a proposed medication or proposed medication dosage conflicts with a current medication or current medication dosage associated with the at least one patient.

9. The system of claim 1, wherein the data provided by the health coach module comprises information for supporting patient treatment compliance to chronic illness-specific treatment guidelines selected by at least one of the at least one medical professional and the at least one health coach.

10. The system of claim 1, wherein the data received by the patient module comprises information provided by the at least one patient through the network from at least one of a health monitoring device, mobile electronic device, and user computer.

11. The system of claim 1, wherein the data received by the patient module comprises at least one visual representation of the clinical health condition of the at least one patient.

12. The system of claim 1, wherein the patient module is further adapted for tracking use of patient-specific curriculum by the at least one patient.

13. The system of claim 1, wherein the patient module is further adapted for tracking communication between the at least one patient and at least one of another patient, the at least one medical professional, and the at least one health coach.

14. The system of claim 1, wherein each of the medical professional module, health coach module, patient module, and public health module is operatively associated with a graphical user interface comprising controls for selectively receiving, storing, and providing data in the system in response to an action by at least one of the at least one medical professional, the at least one health coach, the at least patient, and the at least one research professional.

15. The system of claim 10, wherein the at least one health monitoring device is a heart rate monitor, blood pressure meter, peak flow meter, pulse oximeter, pedometer, weighing scale, or glucometer.

16. The system of claim 11, wherein the at least one visual representation comprises at least one of graphs and charts associated with the clinical health condition of the at least one patient.

17. A method of using a computerized system-programmed for providing care support to at least one patient having at least one chronic illness, comprising the steps of:
(a) accessing the computerized system through a network, the computer system comprising a server comprising:
  (i) a medical professional module adapted for receiving, storing, and providing data in communication with at least one medical professional at the point of care, wherein the medical professional module comprises at least one algorithm for generating at least one care decision for the at least one patient at the point of care, wherein the at least one algorithm is based at least in part on at least one of disease-specific national diagnostic guidelines, disease-specific national treatment guidelines, patient-specific medication plans, and clinical care pathways;
  (ii) a health coach module adapted for receiving, storing, and providing data in communication with the at least one patient and at least one health coach;
  (iii) a patient module adapted for receiving, storing, and providing data in communication with the at least one patient; and
  (iv) a public health module adapted for receiving, storing, and providing data in communication with at least one research professional, wherein the public health module is adapted for generating cost-benefit information associated with at least one treatment decision for a chronic illness selected by at least one of the at least one medical professional and at least one health coach,
wherein the server and each of the medical professional module, health coach module, patient module, and public health module are operatively associated with a corresponding one of the at least one medical professional, the at least one health coach, the at least one patient, and the at least one research professional through a network computing system to perform for interacting with at least one user of the system programmed for providing care support to at least one patient having at least one chronic illness;
(b) providing identification designating that the user is a medical professional, health coach, patient, or research professional; and
(c) performing at least one of the steps of:
  (i) providing data comprising at least one of information from electronic medical records associated with the at least one patient, information associated with at least one treatment compliance program for treating the at least one chronic illness, and information associated with the clinical health condition of the at least one patient;
  (ii) receiving an alert when a proposed medication or proposed medication dosage conflicts with a current medication or current medication dosage associated with the at least one patient;
  (iii) receiving data for supporting patient treatment compliance to chronic illness-specific treatment guidelines selected by at least one of the at least one medical professional and the at least one health coach;
  (iv) providing data through the network from at least one of a health monitoring device, mobile electronic device, and user computer;
  (v) tracking use of patient-specific curriculum by the at least one patient;
  (vi) tracking communication between each of the at least one patient and at least one of another patient, the medical professional, and the health coach;
  (vii) generating cost-benefit information associated with at least one treatment decision for a chronic illness selected by at least one of the at least one medical professional and at least one health coach;
  (viii) analyzing patient-specific data; and
  (xi) receiving data associated with at least one clinical health trial.

18. A method of using a computerized system programmed for providing care support to at least one patient having at least one chronic illness, comprising the steps of:
(a) accessing the computerized system through a network; the computer system comprising a server comprising:
  (i) a medical professional module adapted for receiving, storing, and providing data in communication with at least one medical professional at the point of care, wherein the medical professional module comprises at least one algorithm for generating at least one care decision for the at least one patient at the point of care, wherein the at least one algorithm is based at least in part on at least one of disease-specific national diagnostic guidelines, disease-specific national treatment guidelines, patient-specific medication plans, and clinical care pathways;
  (ii) a health coach module adapted for receiving, storing, and providing data in communication with the at least one patient and at least one health coach;
  (iii) a patient module adapted for receiving, storing, and providing data in communication with the at least one patient; and
  (iv) a public health module adapted for receiving, storing, and providing data in communication with at least one research professional, wherein the public health module is adapted for generating cost-benefit information associated with at least one treatment decision for a chronic illness selected by at least one of the at least one medical professional and at least one health coach,
wherein the server and each of the medical professional module, health coach module, patient module, and public health module are operatively associated with a corresponding one of the at least one medical professional, the at least one health coach, the at least one patient, and the at least one research professional through a network computing system to perform for interacting with at least one user of the system programmed for providing care support to at least one patient having at least one chronic illness;
(b) providing identification designating that the user is a medical professional; and
(c) performing at least one of the steps of:
  (i) providing data that comprises at least one of information from electronic medical records associated with the at least one patient, information associated with at least one treatment compliance program for treating the at least one chronic illness, and information associated with the clinical health condition of the at least one patient;
  (ii) receiving an alert when a proposed medication or proposed medication dosage conflicts with a current medication or current medication dosage associated with the at least one patient.

19. The method of claim 18, further comprising the step of:
(d) generating at least one care decision for the at least one patient with a chronic illness at the point of care.

20. A method of using a computerized system programmed for providing care support to at least one patient having at least one chronic illness, comprising the steps of:

(a) accessing the computerized system through a network connection; the computer system comprising a server comprising:
  (i) a medical professional module adapted for receiving, storing, and providing data in communication with at least one medical professional at the point of care, wherein the medical professional module comprises at least one algorithm for generating at least one care decision for the at least one patient at the point of care, wherein the at least one algorithm is based at least in part on at least one of disease-specific national diagnostic guidelines, disease-specific national treatment guidelines, patient-specific medication plans, and clinical care pathways;
  (ii) a health coach module adapted for receiving, storing, and providing data in communication with the at least one patient and at least one health coach;
  (iii) a patient module adapted for receiving, storing, and providing data in communication with the at least one patient; and
  (iv) a public health module adapted for receiving, storing, and providing data in communication with at least one research professional, wherein the public health module is adapted for generating cost-benefit information associated with at least one treatment decision for a chronic illness selected by at least one of the at least one medical professional and at least one health coach,
  wherein the server and each of the medical professional module, health coach module, patient module, and public health module is operatively associated with a corresponding one of the at least one medical professional, the at least one health coach, the at least one patient, and the at least one research professional through a network computing system to perform for interacting with at least one user of the system programmed for providing care support to at least one patient having at least one chronic illness;
(b) providing identification designating that the user is a health coach; and
(c) performing at least one of the steps of:
  (i) receiving data for supporting patient treatment compliance to chronic illness-specific treatment guidelines selected by at least one of the medical professional and health coach;
  (ii) tracking use of patient-specific curriculum by the at least one patient; and
  (iii) tracking communication between each of the at least one patient and at least one of another patient, the at least one medical professional, and the at least one health coach.

21. The method of claim 20, further comprising the step of:
(d) generating at least one decision associated with patient treatment compliance for the at least one patient with a chronic illness.

22. A method of using a the computerized system programmed for providing care support for at least one patient having at least one chronic illness, comprising the steps of:
  (a) accessing the computerized system through a network; the computer system comprising a server comprising:
    (i) a medical professional module adapted for receiving, storing, and providing data in communication with at least one medical professional at the point of care, wherein the medical professional module comprises at least one algorithm for generating at least one care decision for the at least one patient at the point of care, wherein the at least one algorithm is based at least in part on at least one of disease-specific national diagnostic guidelines, disease-specific national treatment guidelines, patient-specific medication plans, and clinical care pathways;
    (ii) a health coach module adapted for receiving, storing, and providing data in communication with the at least one patient and at least one health coach;
    (iii) a patient module adapted for receiving, storing, and providing data in communication with the at least one patient; and
    (iv) a public health module adapted for receiving, storing, and providing data in communication with at least one research professional, wherein the public health module is adapted for generating cost-benefit information associated with at least one treatment decision for a chronic illness selected by at least one of the at least one medical professional and at least one health coach,
    wherein the server and each of the medical professional module, health coach module, patient module, and public health module are operatively associated with a corresponding one of the at least one medical professional, the at least one health coach, the at least one patient, and the at least one research professional through a network computing system to perform for interacting with at least one user of the system programmed for providing care support to at least one patient having at least one chronic illness;
  (b) providing identification designating that the user is the at least one patient;
  (c) performing at least one of the steps of:
    (i) providing data associated with the clinical health condition of the at least one patient through the network from at least one of a health monitoring device, mobile electronic device, and user computer;
    (ii) viewing at least one visual representation of the clinical health condition of the at least one patient;
    (iii) viewing patient-specific curriculum; and
    (iv) communicating with at least one of another patient, the at least one medical professional, and the at least one health coach through the network.

23. The method of claim 22, wherein the step of communicating with at least one of another patient, the at least one medical professional, and the at least one health coach through the network connection comprises at least one of the steps of receiving, generating, and sending at least one of an SMS text message, electronic mail message, and social networking message.

24. A software product comprising a non-transitory computer-readable medium in which computer program instructions are stored, said instructions, when executed by a computing system, cause the computing system to perform the acts of:
  (a) receiving, storing, and providing data in communication with at least one medical professional;
  (b) receiving, storing, and providing data in communication with at least one health coach;
  (c) receiving, storing, and providing data in communication with at least one patient having at least one chronic illness;
  (d) receiving, storing, and providing data in communication with at least one research professional;
  (e) facilitating interactions between each of the at least one medical professional, the at least one health coach, the at least one patient, and the at least one research professional; and
  (f) providing care support to the at least one patient, wherein the software comprises at least one algorithm for generating at least one care decision for the at least one patient at the point of care and at least one visual representation of the clinical health condition of the at least one patient, wherein the at least one algorithm is based at least in part on at least one of disease-specific national diagnostic guidelines, disease-specific national treatment guidelines, patient-specific medication plans, and clinical care pathways.

25. A method of using a computerized system programmed for providing care support to at least one patient having at least one chronic illness, comprising:
 (a) providing a computerized system programmed for providing care support to at least one patient having at least one chronic illness, comprising:
  (i) a first computer software implemented means for receiving, storing, and providing data in communication with at least one medical professional at the point of care;
  (ii) a second computer software implemented means for receiving, storing, and providing data in communication with the at least one patient and at least one health coach;
  (iii) a third computer software implemented means for receiving, storing, and providing data in communication with the at least one patient; and
  (iv) a fourth computer software implemented means for receiving, storing, and providing data in communication with at least one research professional,
  wherein each of the computer software implemented means is operatively associated with a user corresponding to at least one of the at least one medical professional, at least one health coach, at least one patient, and at least one research professional through a network,
  wherein the computer-software implemented means comprises software comprising a non-transitory computer-readable storage medium in which computer program instructions comprise at least one algorithm, including instructions, which, when executed by a computing system, cause the computing system to perform functions for interacting with the at least one user of the system and to provide care support to at least one patient having at least one chronic illness, wherein the at least one algorithm is based at least in part on at least one of disease-specific national diagnostic guidelines, disease-specific national treatment guidelines, patient-specific medication plans, and clinical care pathways;
 (b) causing at least one of the computer software implemented means to perform at least one of the functions of receiving data, storing data, and providing data; and
 (c) causing at least one of the computer software implemented means to generate at least one care decision for a chronic illness from the at least one medical professional to the at least one patient at the point of care and to display at least one visual representation of the health condition of the at least one patient.

* * * * *